(12) United States Patent
Knesel et al.

(10) Patent No.: US 8,119,363 B2
(45) Date of Patent: Feb. 21, 2012

(54) CELL SAMPLE PREPARATION METHOD AND APPARATUS

(75) Inventors: Ernest A. Knesel, Greensboro, NC (US); Bradley W. Knesel, Kernersville, NC (US); Joel C. Dry, McLeansville, NC (US); Kevin J. Rackers, Summerfield, NC (US); Robert M. Hicks, Jr., Danville, VA (US); Benjamin A. Perrot, Greensboro, NC (US)

(73) Assignee: CellSolutions, LLC, Greensboro, NC (US)

( * ) Notice: Subject to any disclaimer, the term of this patent is extended or adjusted under 35 U.S.C. 154(b) by 964 days.

(21) Appl. No.: 12/114,155

(22) Filed: May 2, 2008

(65) Prior Publication Data

US 2009/0275076 A1  Nov. 5, 2009

(51) Int. Cl.
 *C12Q 1/08* (2006.01)
(52) U.S. Cl. .......................................... 435/40; 435/7.1
(58) Field of Classification Search ........................ None
See application file for complete search history.

(56) References Cited

U.S. PATENT DOCUMENTS

| | | | |
|---|---|---|---|
| 4,863,852 A | | 9/1989 | Wilkins et al. |
| 5,346,831 A | * | 9/1994 | Carrico et al. ................. 436/174 |
| 5,677,966 A | * | 10/1997 | Doerrer et al. ................. 382/128 |
| 6,562,299 B1 | | 5/2003 | Ostgaard et al. |
| 6,572,824 B1 | | 6/2003 | Ostgaard et al. |
| 7,595,874 B1 | * | 9/2009 | Pelekhaty et al. ............ 356/318 |
| 2003/0215936 A1 | | 11/2003 | Kallioniemi et al. |
| 2005/0250211 A1 | | 11/2005 | Reinhardt et al. |
| 2009/0155841 A1 | * | 6/2009 | Yamasaki ................. 435/40.51 |

* cited by examiner

*Primary Examiner* — Hope Robinson

(74) *Attorney, Agent, or Firm* — Withrow & Terranova, P.L.L.C.

(57) ABSTRACT

An apparatus and method for automatic thin-layer cell sample slide preparation without requiring human intervention are disclosed. According to one embodiment, a cell sample is measured to derive a cell sample measurement. An estimation of total cellularity of the cell sample is determined based upon the cell sample measurement. A differential volume of diluent is dispensed to the cell sample based upon the estimation of total cellularity of the cell sample to form a cell suspension. In one embodiment, a differential volume of the cell suspension and a differential volume of cell adherent may be combined based upon the estimation of total cellularity of the cell sample to form a cell mixture. A differential volume of the cell suspension or cell mixture (if an adherent is mixed with the cell suspension) is dispensed onto a surface of a sample slide.

23 Claims, 29 Drawing Sheets

CELL SAMPLE PREPARATION METHOD AND APPARATUS

FIELD OF THE INVENTION

The present invention is a method and apparatus for thin-layer cell sample slide preparation. More particularly, the present invention provides automated thin-layer cell sample slide preparation through a series of variable dilutions based upon cellularity of the cell sample without compromising the initial cell sample.

BACKGROUND OF THE INVENTION

Conventional cell preparation for tests, such as the conventional Pap smear, involve direct application of cellular material to a glass slide which is subsequently processed, screened, and diagnosed by trained professionals. Other methods for preparing cell samples for analysis involve pre-processing of the cell sample prior to application to the slide. Exemplary conventional pre-processing includes vacuum filter deposition onto a slide, electrical charge-based deposition using covalent bonds between the slide and the cells, and manual dilution of the cell sample and manual deposition to the slide. The pre-processing is performed so that when cells are applied to the slide the cells are distributed in a thin layer which allows for a more optimal presentation for diagnostics. In some of these thin-layer methods centrifugation is used to separate cells from other portions (e.g., the supernatant) of the cell sample within a centrifugation tube. Because the cells are heavier than the other portions of the sample, the cells form a pellet in the bottom of the centrifugation tube. The supernatant is then poured off from the centrifuge tube to leave the cell pellet. Samples of the cells within the cell pellet can then be manually prepared on glass slides for analysis by a trained professional.

Manual methods and systems for preparing cell samples on slides rely on visual observation of the cell pellet within the centrifuge tube to make a very crude estimate of the size of the cell pellet. A diluent, such as water, is added to the centrifuge tube to re-suspend the cells, thereby forming a cell suspension. The visual observation of the cell pellet is inconsistent and may not provide an accurate indication of cell pellet size. Consequently, the amount of diluent added based upon this inaccurate and inconsistent observation may also be inconsistent. As a result of human error inherent in a conventional manual method, the cellularity (e.g., the number of cells suspended within the cell suspension) is inconsistent, and thus the prepared sample is inconsistent from one slide to the next.

The actual slide samples are prepared by drawing an amount of the cell suspension from the original centrifuge tube into a pipette. Then an amount of the cell suspension is dispensed by dropping the cell suspension from the pipette from a height above the slide. This procedure is performed by hand and results in inaccuracies and poorly prepared slides.

The inconsistent cellularity of the cell mix coupled with the uncontrolled dispensing results in inconsistent cell samples being placed on the slides for analysis. For example, slides are often prepared with areas that have too many or too few cells per unit area. These areas are often unusable and often render the entire slide unusable for any meaningful analysis. If the slide is unusable, the problem is further complicated if the original sample has been compromised as describe above. This could necessitate a recollection of the sample from the patient.

Accordingly, there exists a need to provide a method and system for thin-layer cell sample slide preparation yielding uniform cell samples through a series of variable dilutions based upon cellularity of the cell sample without compromising the initial cell sample.

SUMMARY OF THE INVENTION

Embodiments of the present invention include a method and apparatus for automated thin-layer cell sample slide preparation. More particularly, embodiments of the present invention provide thin-layer cell sample slide preparation through a series of automated variable dilutions based upon cellularity of the cell sample without compromising the initial cell sample and without requiring human intervention. Automated sample tracking can be provided at each stage of processing to track the cell sample through the automated thin-layer cell sample slide preparation. A quantitative cellularity assessment may first be performed on a cell pellet to determine a cellularity estimate for the cell sample. A differential volume of cell dilution may be performed based upon the assessed cellularity estimate which re-suspends the cells from the cell pellet to form a cell suspension according to a predetermined cell concentration. The cell suspension can then be transferred to a transfer tube or other holder. A variable volume of the cell suspension may then be transferred to a slide such that a thin layer of the cell suspension is deposited on the slide to form a sample cell slide preparation to assist with cell analysis.

The method may be implemented via an automated continuous multi-sample sequential cytology thin-layer slide preparation system. In an embodiment of the present invention, a conveyor subsystem moves cell samples within centrifuge tubes through the system. A pellet size reader subsystem quantitatively determines the cellularity of the cell sample within the centrifuge tubes. A bar-code tracking and labeling subsystem tracks the cell sample through the automated thin-layer cell sample slide preparation. A fluid control subsystem operates as a pump and syringe system to dispense and transfer fluids, respectively, at different stages of processing, including pattern dispensing of the cell mixture to a slide to create the thin-layer cell sample. A cell-sample drying subsystem dries the prepared thin-layer cell sample slides for analysis.

Quantitative cellularity assessment can be performed, for example, by ultrasonic or photometric sensing, to determine an estimate of the cellularity of a cell pellet within the centrifuge tube. A differential cell dilution is performed within the centrifuge tube based upon the estimate of cellularity by adding a differential volume of diluent to the tube to re-suspend the cells and form a cell suspension according to a predetermined concentration. The volume of cell dilution may be such that a predetermined cell concentration is formed. The diluent may be, for example, water, saline, buffered saline, or a similar substance.

In embodiments of the present invention, an optional adherent may also be used to facilitate adhering the cell suspension to a sample side. The adherent may be applied or pre-applied to the sample slide, or may be mixed with the cell suspension, wherein the resulting cell mixture is dispensed to the sample slide. If the later option is chosen, then based on the estimate of cellularity, a differential volume of the cell suspension may be transferred to a transfer tube and mixed with a differential volume of cell adherent to form a cell mixture having a consistent cellularity within the transfer tube. A variable amount of the cell mixture is deposited via close-proximity cell deposition to a slide to form a thin layer of cells. The thin-layer slide preparation facilitates faster drying and provides a flexibility of user applications for analysis. For example, the close-proximity cell deposition may be performed as a pattern to allow sequential cell analysis, such as a square or rectangular pattern, a circular pattern, or other two dimensional patterns. The system maintains positive cell sample identification throughout sample preparation. The present invention does not require and is not limited to use of any adherent.

In embodiments of the present invention, a cell-sample drying subsystem may be used to dry the prepared thin-layer cell sample slides for analysis. A stacked tray system for prepared samples can be used to align the cell samples within trays which are stacked to conserve space. Forced air can be supplied to the trays via air inlets on the stacked trays. Air outlets are located opposite the air inlets on the trays such that the forced air flows across the trays within the stack to expedite drying. The air may also be treated (e.g., heated or dehumidified) to facilitate drying, based upon the ambient air conditions within the environment surrounding the automated continuous multi-sample sequential cytology thin-layer slide preparation system.

Those skilled in the art will appreciate the scope of the present invention and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the invention, and together with the description serve to explain the principles of the invention.

DETAILED DESCRIPTION OF THE PREFERRED EMBODIMENTS

Figure 1:
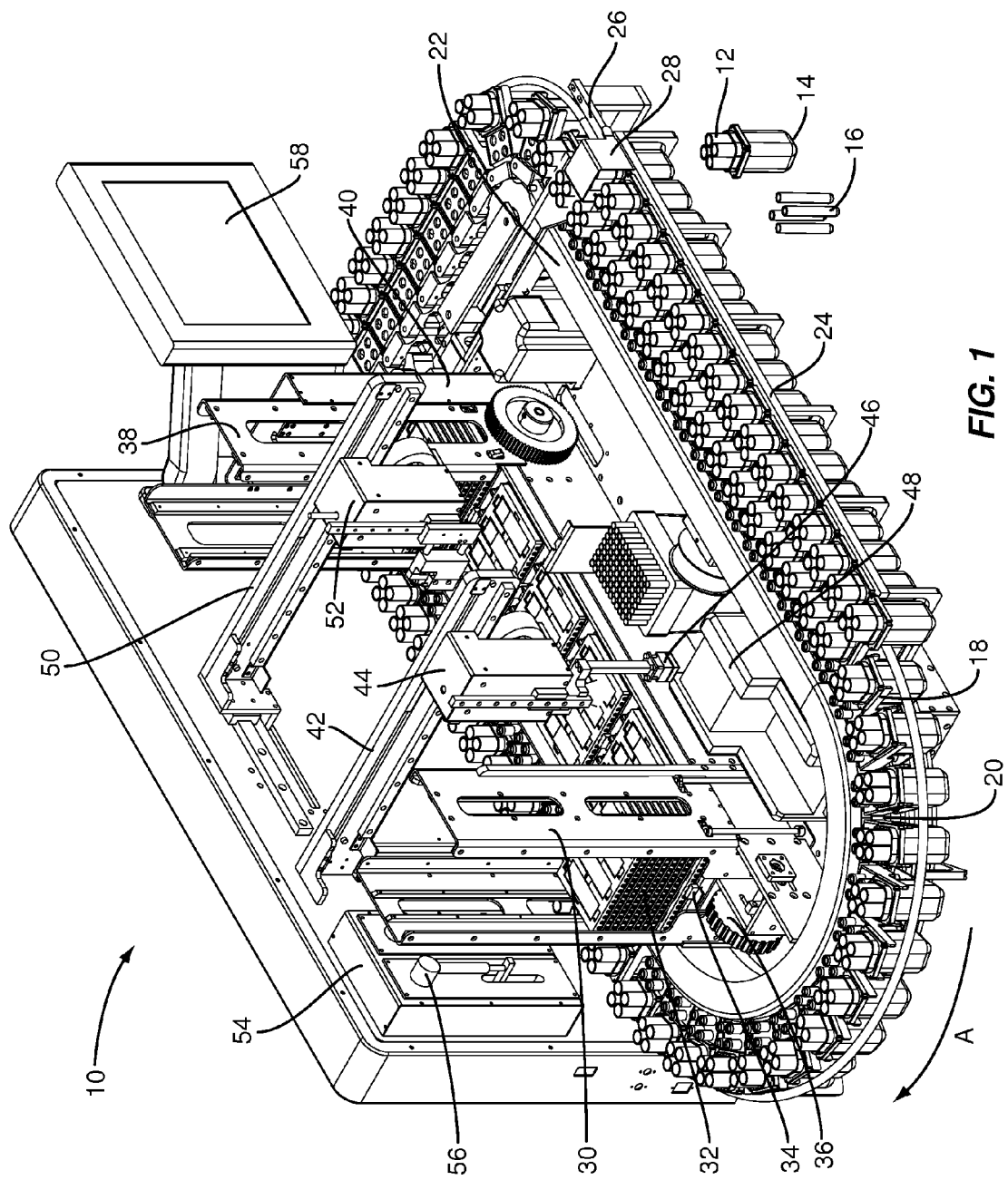
FIG. 1 illustrates an exemplary automated continuous multi-sample sequential cytology thin-layer slide preparation system capable of automatically preparing and tracking cell samples without human intervention as they are deposited to slides for analysis, according to an embodiment of the subject matter described herein.

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

Embodiments of the present invention include a method and apparatus for automated thin-layer cell sample slide preparation. More particularly, embodiments of the present invention provide thin-layer cell sample slide preparation through a series of automated variable dilutions based upon cellularity of the cell sample without compromising the initial cell sample and without requiring human intervention. Automated sample tracking can be provided at each stage of processing to track the cell sample through the automated thin-layer cell sample slide preparation. A quantitative cellularity assessment may first be performed on a cell pellet to determine a cellularity estimate for the cell sample. A differential volume of cell dilution may be performed based upon the assessed cellularity estimate which re-suspends the cells from the cell pellet to form a cell suspension according to a predetermined cell concentration. The cell suspension can then be transferred to a transfer tube or other holder. A variable volume of the cell suspension may then be transferred to a slide such that a thin layer of the cell suspension is deposited on the slide to form a sample cell slide preparation to assist with cell analysis.

The method may be implemented via an automated continuous multi-sample sequential cytology thin-layer slide preparation system. In an embodiment of the present invention, a conveyor subsystem moves cell samples within centrifuge tubes through the system. A pellet size reader subsystem quantitatively determines the cellularity of the cell sample within the centrifuge tubes. A bar-code tracking and labeling subsystem tracks the cell sample through the automated thin-layer cell sample slide preparation. A fluid control subsystem operates as a pump and syringe system to dispense and transfer fluids, respectively, at different stages of processing, including pattern dispensing of the cell mixture to a slide to create the thin-layer cell sample. A cell-sample drying subsystem dries the prepared thin-layer cell sample slides for analysis.

Quantitative cellularity assessment can be performed, for example, by ultrasonic or photometric sensing, to determine an estimate of the cellularity of a cell pellet within the centrifuge tube. A differential cell dilution is performed within the centrifuge tube based upon the estimate of cellularity by adding a differential volume of diluent to the tube to re-suspend the cells and form a cell suspension. The volume of cell dilution may be such that a predetermined cell concentration is formed. The diluent may be, for example, water, saline, buffered saline, or a similar substance.

In embodiments of the present invention, an optional adherent may also be used to facilitate adhering the cell suspension to a sample side. The adherent may be applied or pre-applied to the sample slide, or may be mixed with the cell suspension, wherein the resulting cell mixture is dispensed to the sample slide. If the later option is chosen, then based on the estimate of cellularity, a differential volume of the cell suspension may be transferred to a transfer tube and mixed with a differential volume of cell adherent to form a cell mixture having a consistent cellularity within the transfer tube. A variable amount of the cell mixture is deposited via close-proximity cell deposition to a slide to form a thin layer of cells. The thin-layer slide preparation facilitates faster drying and provides a flexibility of user applications for analysis. For example, the close-proximity cell deposition may be performed as a pattern to allow sequential cell analysis, such as a square or rectangular pattern, a circular pattern, or other two dimensional patterns. The system maintains positive cell sample identification throughout sample preparation. The present invention does not require and is not limited to use of any adherent.

In embodiments of the present invention, a cell-sample drying subsystem may be used to dry the prepared thin-layer cell sample slides for analysis. A stacked tray system for prepared samples can be used to align the cell samples within trays which are stacked to conserve space. Forced air can be supplied to the trays via air inlets on the stacked trays. Air outlets are located opposite the air inlets on the trays such that the forced air flows across the trays within the stack to expedite drying. The air may also be treated (e.g., heated or dehumidified) to facilitate drying, based upon the ambient air conditions within the environment surrounding the automated continuous multi-sample sequential cytology thin-layer slide preparation system.

FIG. 1 illustrates an exemplary automated continuous multi-sample sequential cytology thin-layer slide preparation system 10 (hereinafter "system 10") capable of automatically preparing and tracking cell samples without human intervention as they are processed and deposited to slides for analysis. The system 10 automates the process for thin-layer cell sample slide preparation described herein.

The thin-layer cell sample process, which is automated by and described in association with the system 10, will be described in detail beginning with FIG. 2 below. However, in order to better understand the automation provided by the system 10 and the process of thin-layer cell sample slide preparation described within FIG. 2, the system 10 is described from a high-level perspective to provide a better context within which the processing of FIG. 2 may be implemented. Sample tubes 12 are loaded into a tube rack 14 and centrifuged prior to operation of the cell sample slide preparation process. During the centrifugation process, heavier components of a sample collect at the bottom of the sample tubes 12. The components of the sample tubes 12 include, among other things, cells, natural mucus, and other fluids which are gathered during sample collection. The cells within the sample are typically the heaviest components of the sample. As such, the cells collect at the bottom of the sample tubes 12 and form a cell pellet. A supernatant, which is lighter than the cell pellet and which includes the natural mucus and other fluids gathered during cell collection, will be suspended above the cell pellet. The supernatant may then be poured from the sample tubes 12 to leave only the cell pellets within the sample tubes 12. After the supernatant is poured from the sample tubes 12 and the sample tubes are placed within the system 10, the process for thin-layer cell sample slide preparation is automated and performed without human intervention.

The sample tubes 12 will each be labeled with sample indicia that identify and correlate the sample contained within the sample tubes 12 with a patient for analysis tracking purposes. The tube racks 14, including the sample tubes 12 having the cell pellets at the bottom and the supernatant poured off, are placed along with transfer tubes 16 into a rack carrier 18 of a tube conveyor 20 at a tube and rack loading area 22. The tube conveyor 20 then rotates in a clockwise direction represented by the arrow A to process cell samples. After the cell samples are processed, the tube racks 14 are moved to a tube discharge track 24 at a location of a rack advance arm 26 by activation of a rack discharge bracket 28. As the rack discharge bracket 28 activates, it moves the tube racks 14 from the rack carriers 18 and onto the tube discharge track 24. As such, the rack carriers 18 are once again available within the tube and rack loading area 22 for new samples.

A tray downstacker 30 provides a location within which cell sample slide trays 32 may be placed by a user of the system 10 and from which the trays 32 are automatically fed through the system 10 for cell sample slide preparation. A belt 34 is driven on a gear 36 to advance the trays 32 from the tray downstacker 30 for cell sample slide preparation and processing. The belt 34 removes one tray 32 at a time from the tray downstacker 30 and moves that tray 32 forward for sample preparation. It should be noted that only a portion of the belt 34 is illustrated at the edge of the bottom tray 32 within the tray downstacker 30 for ease of illustration purposes and that the belt 34 is not illustrated in its entirety to show details of the gear 36 which drives the belt.

After the cell sample slide preparation is completed, the belt 34 continues to move the trays 32 into a tray upstacker 38. The tray upstacker 38 automatically stacks the trays 32 for drying and later retrieval by a user of the system 10. An air discharge chamber 40 provides a positive air pressure at the edge of the trays 32 within the tray upstacker 38. This positive air pressure assists with cell sample drying and will be described in more detail in association with FIGS. 21-25 below. The air discharge chamber 40, in conjunction with the trays 32, provides sample drying capabilities within the system 10.

While the loading of trays 32 to the tray downstacker 30, the unloading of trays from the tray upstacker 38, and the loading and unloading of samples from the tube conveyor 20 and the tube discharge track 24, respectively, are performed by the user of the system 10, the process for thin-layer cell sample slide preparation is automated and performed without human intervention.

Four robotic arms are provided within the system 10. A label handling robotic arm 42 is provided for sample tracking and label placement purposes. In conjunction with the label handling robotic arm 42, a label end effector 44 controls a vacuum foot 46 to retrieve labels from a label printer 48 for cell sample tracking purposes. The label printer 48 may, for example, print barcode labels for use in cell sample tracking, as will be described in more detail below. The label handling robotic arm 42, in conjunction with the label end effector 44, provides a two-axis robotic arm for label handling purposes. The label handling robotic arm 42, in conjunction with the label end effector 44 and the vacuum foot 46, provides label handling capabilities for sample tracking within the system 10.

A fluid handling robotic arm 50 operates in conjunction with a fluid handling end effector 52 to provide fluid control capabilities to process the cell samples, as will be described in more detail beginning with FIG. 2 below. The fluid handling robotic arm 50, in conjunction with the fluid handling end effector 52, provides a three-axis robotic arm for fluid handling purposes. Details of automated fluid handling will begin with FIG. 12 below. Two additional robotic arms are present on the system 10 and will be described in more detail below within FIGS. 7 and 26-28, respectively.

Syringe pumps 54 provide both pumping and vacuum capabilities, selectable via a switch 56, for the dispensing and retrieval of fluids during the thin-layer cell sample slide preparation process. As will be described below beginning with FIG. 12, the syringe pumps 54 are used to dispense a variable volume of diluent, such as water, saline, buffered saline, or a similar substance, to the sample tube 12. The syringe pumps 54 are also used to extract a variable volume of a variably diluted cell suspension from the sample tube 12 and to dispense the variable volume to the transfer tube 16. If an adherent is to be mixed with the cell suspension to form a cell mixture to apply to the sample slide, the syringe pumps 54 may additionally be used to dispense a variable volume of cell adherent to the transfer tube 16. The syringe pumps 54 can then extract a variable volume of the prepared cell mixture from the transfer tube 16 and dispense the prepared cell mixture for analysis. FIG. 2 below details this process. The cell adherent may be chosen from an alcohol solution, including but not limited to an acrylate resin, a gelatin, including but not limited to a Chrome alum gelatin, Albumin, Collagen, Glycerin, Silane (aminialkysilane), Poly-L-lysine, Poly-D-lysine, Poly-L and D-arginine and/or their derivatives, and Polyethylene glycol. The cell adherent may also be provided in the form of chemically modified glass used to make microscope slides. The cell adherent may also be the GluCyte™ cell adherent manufactured and distributed by Synermed Select Partners, Inc. The cell adherent is not limited to any particular type or method of providing.

Note that if transfer tubes 16 are used as is the case in one embodiment of the present invention, their use may be to facilitate an adherent being added to the cell suspension to form the cell mixture. However, if an adherent is not used or an adherent is applied or pre-applied directly to a sample slide rather than being mixed with the cell suspension, there may be no need to transfer the cell suspension from the sample tubes 12 to transfer tubes 16. The cell suspension to be applied to the sample slide may be obtained directly from the sample tubes 12 without need of the transfer tubes 16. Alternatively, the transfer tubes 16 may still be employed in the process of transferring the cell suspension from the sample tubes 12 to the sample slide. In either case, the use of transfer tubes 16 does not necessarily imply or require use of an adherent or mixture of an adherent with the cell suspension prior to dispensing on the sample slide.

A touch-screen monitor and control system 58 allows the user to control and monitor the system 10. The touch-screen monitor and control system 58 may be used by the user of the system 10 for a variety of configuration, setup, monitoring and control activities. As such, all such activities are considered to be within the scope of the subject matter described herein. Additionally, the monitoring and control activities may be partitioned into multiple monitoring and control subsystems without departure from the scope of the subject matter described herein. It should further be noted that after the system 10 is configured by a user via the touch-screen monitor and control system 58, the process for thin-layer cell sample slide preparation is automated and performed without human intervention.

Figure 2:
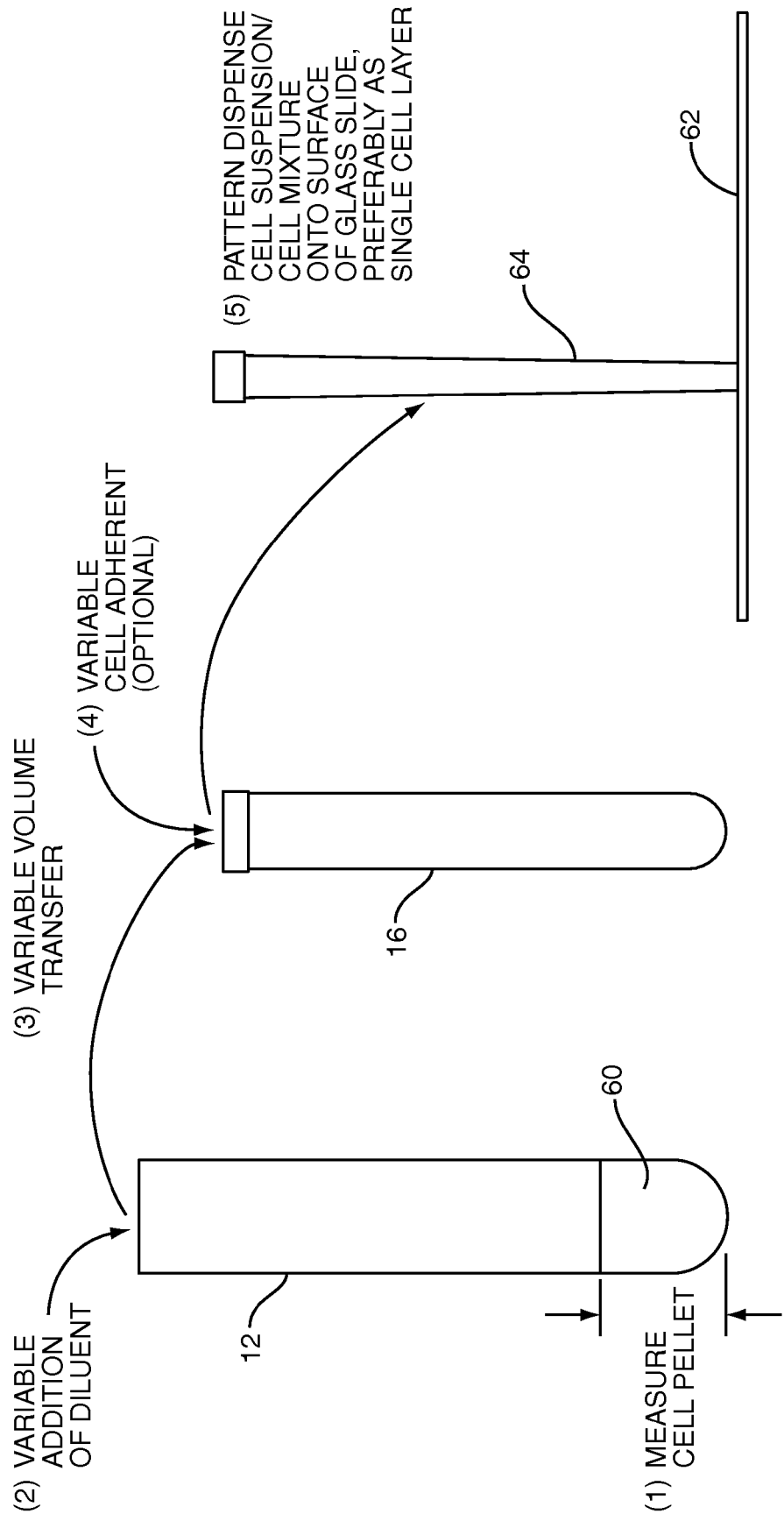
FIG. 2 illustrates an exemplary process by which thin-layer cell sample slide preparation is achieved, according to an embodiment of the subject matter described herein.

FIG. 2 illustrates an exemplary process by which thin-layer cell sample slide preparation is achieved according to an embodiment of the present invention. Embodiments allow the cell sample to be provided on the sample slide to form a uniform or substantially uniform thin-layer cell sample slide preparation. The sample tube 12 is shown to include a cell pellet 60. The process begins by measuring a height of the cell pellet 60 (step 1) to determine a quantitative estimate of cellularity for the cell pellet 60. Cellularity, as used herein, may be considered an estimate of the quantity of cells within the cell pellet 60. The estimate of cellularity is used throughout the processes described herein to derive a consistent cell mixture through a series of variable dilutions and additions of substances, such as a cell adherent, to form the cell mixture. As will be described in more detail below, the height of the cell pellet 60 may be measured by ultrasonic, photometric, or other sensing to perform the quantitative cellularity assessment for the cell pellet 60 and to derive the quantitative cellularity estimate for the cell pellet 60. Based upon the quantitative cellularity estimate, a differential volume of diluent, such as water, saline, buffered saline, or a similar substance, is added to the sample tube 12 (step 2) to re-suspend cells within the cell pellet 60 to form a cell suspension. A differential or variable dilution is a volume added that provides a predetermined concentration after dilution occurs. A differential or variable volume is a volume that provides a predetermined concentration after the volume is added. Thus, a differential or variable volume of diluent is a volume of diluent that produces a predetermined cell concentration of the cell sample when the diluent is added to the cell sample, such as the cell pellet 60.

Based on the estimate of cellularity, a volume of the cell suspension is transferred to the transfer tube 16 (step 3). As an optional step, a differential or variable volume of cell adherent can be added to the transfer tube 16 to form a cell mixture having a consistent cellularity within the transfer tube 16 (step 4). A cell adherent facilitates binding or adherence of the cell solution to the sample slide so that the cell solution is not compromised by running off or otherwise escaping from the sample slide prior to analyzation. A differential or variable volume of cell adherent is a volume of cell adherent that allows a thin-layer of the cell mixture to adhere to the sample slide and according to a desired cell concentration such that the adherent does not compromise the cell mixture. In this embodiment, the cell adherent is added to the cell suspension to form a cell mixture. In this manner, the cell adherent is mixed with the cell mixture when dispensed to a sample slide (see step 5 below). Alternatively, the cell adherent may be applied separately to the sample slide without being mixed with the cell suspension prior to dispensing of the cell suspension onto the sample slide. The cell adherent may be pre-applied to the sample slides before the cell suspension is dispensed to the sample slide, or the cell adherent may be applied to the cell suspension after the cell suspension is dispensed onto the sample slide. Although it may be desirable to use a cell adherent to facilitate adherence of the cell suspension or mixture to the sample slide, such is not required. Also note that if a cell adherent is used and mixed with the cell suspension, the order of these steps may be switched, with the variable volume of cell adherent added first, followed by the transfer of the variable quantity of cell mixture.

A variable quantity of the cell mixture can then be aspirated from the transfer tube 16 and dispensed in a pattern directly onto a surface of a glass slide 62 by use of a pipette 64 to form a single cell layer in a selectable pattern onto the surface of the glass slide 62 (step 5). FIGS. 18A-18D below illustrate exemplary patterns via which thin cell layers may be dispensed onto the surface of the glass slide 62. By use of the processes described herein, analysis of cell samples may be improved by eliminating problems with conventional cell sample preparation techniques, such as inconsistent cell distribution and excessive cell voids within prepared cell samples which occurs when inconsistent samples are prepared and dispensed. The process described herein can also maintain the integrity of the original cell sample for subsequent or follow-up testing by not compromising the original cell sample with cell adherent, if used and mixed with the cell solution/sample.

Figure 3:
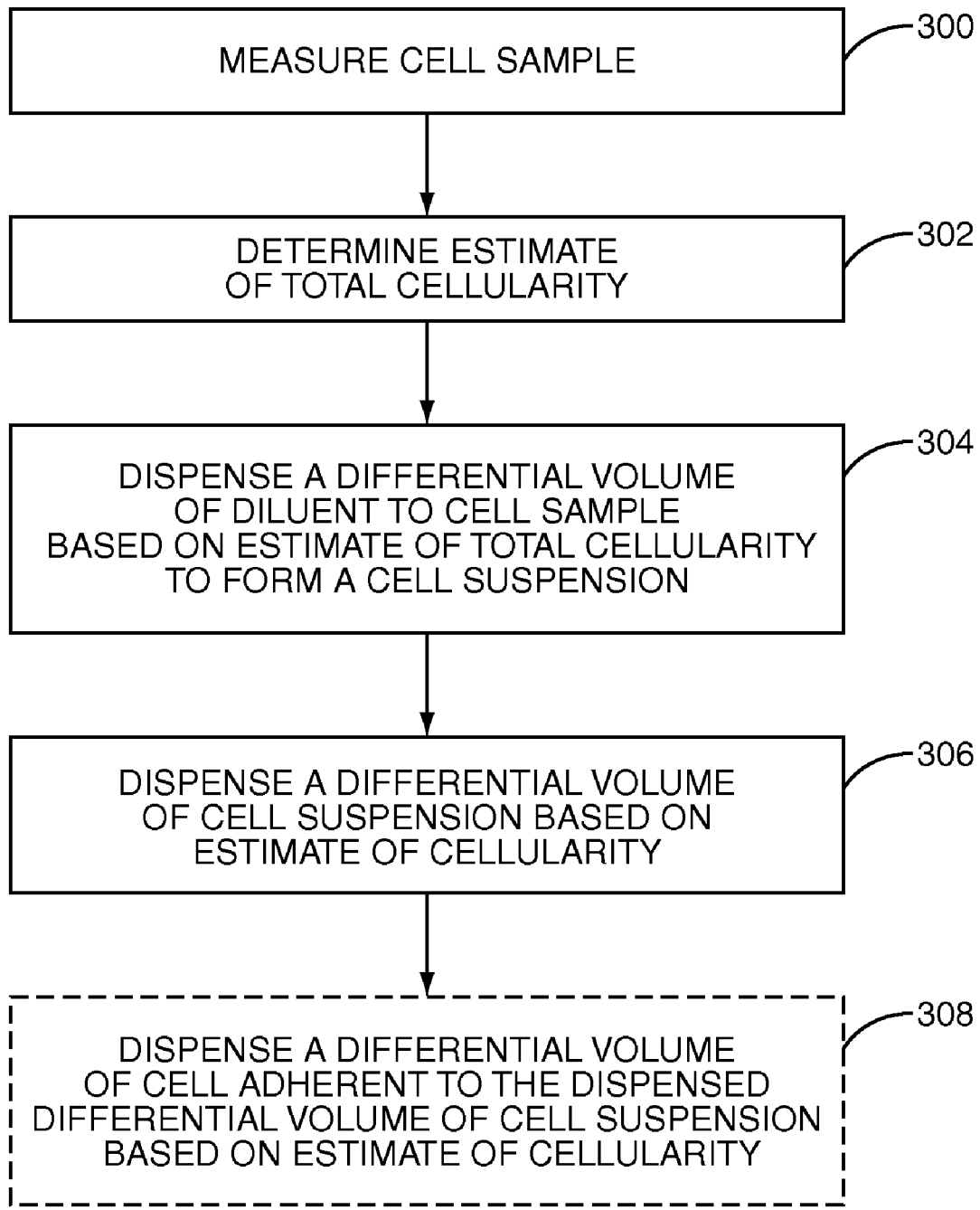
FIG. 3 illustrates an exemplary flow chart illustrating the process described in FIG. 2, according to an embodiment of the subject matter described herein.

FIG. 3 illustrates an exemplary flow chart illustrating the process described above in FIG. 2. The process begins by measuring the cell sample (step 300). For example, the height of the cell pellet 60 within the sample tube 12 may be measured. The process then determines an estimate of the total cellularity within the cell sample (step 302). The process dispenses a differential volume of diluent to the cell sample based upon the estimate of total cellularity to form a cell suspension (step 304). For example, a differential volume of diluent, such as water, saline, buffered saline, or a similar substance, may be added to the sample tube 12 to re-suspend cells within the cell pellet 60 to form the cell suspension. The process then dispenses a differential volume of the cell suspension based on the cellularity estimate (step 306). As described above, the differential volume of the cell suspension may be dispensed based on the cellularity estimate to the transfer tube 16. As an optional step as previously discussed above, the process can then dispense a differential volume of cell adherent to the dispensed differential volume of cell suspension based on the estimate of cellularity (step 308). The order of these steps may be altered without deviation from the scope and content of the subject matter described herein. By dispensing a variable volume at each step based upon the cellularity estimate, the process described within FIG. 3 derives a consistent cell mixture that is then dispensed directly to a glass slide 62 in a pattern as a thin-layer cell sample for ease of analysis. Details of an exemplary algorithm that may be used to determine the differential volumes to transfer at the various stages of processing are described in association with FIG. 7 below.

Figure 4:
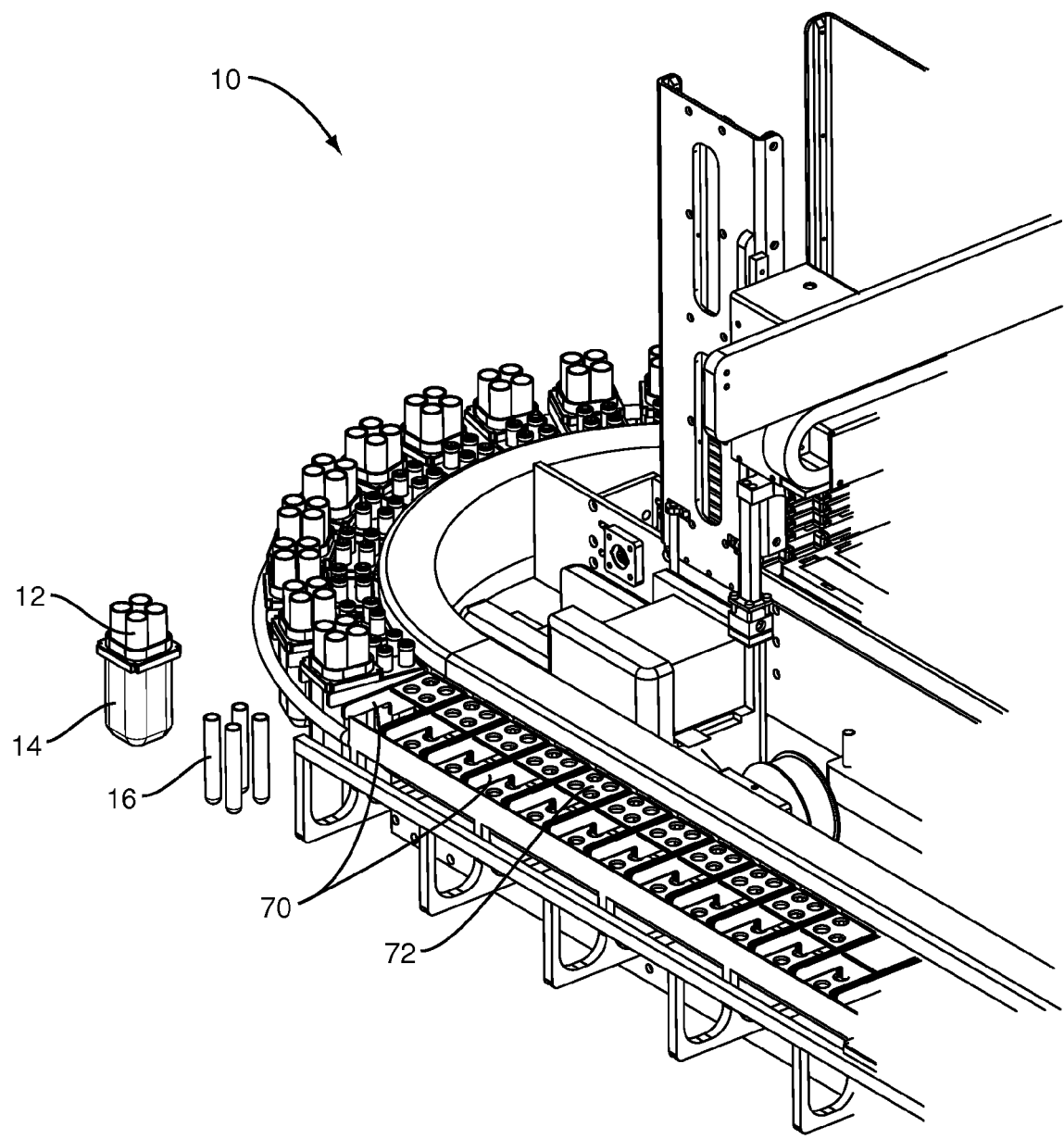
FIG. 4 illustrates details of an exemplary tube conveyor, according to an embodiment of the subject matter described herein.

FIG. 4 illustrates details of the exemplary tube conveyor 20. Each of the rack carriers 18 include two rack support arms 70 for supporting the tube racks 14 and transfer tube support brackets 72 capable of supporting four transfer tubes 16 in association with each tube rack 14.

Figure 5:
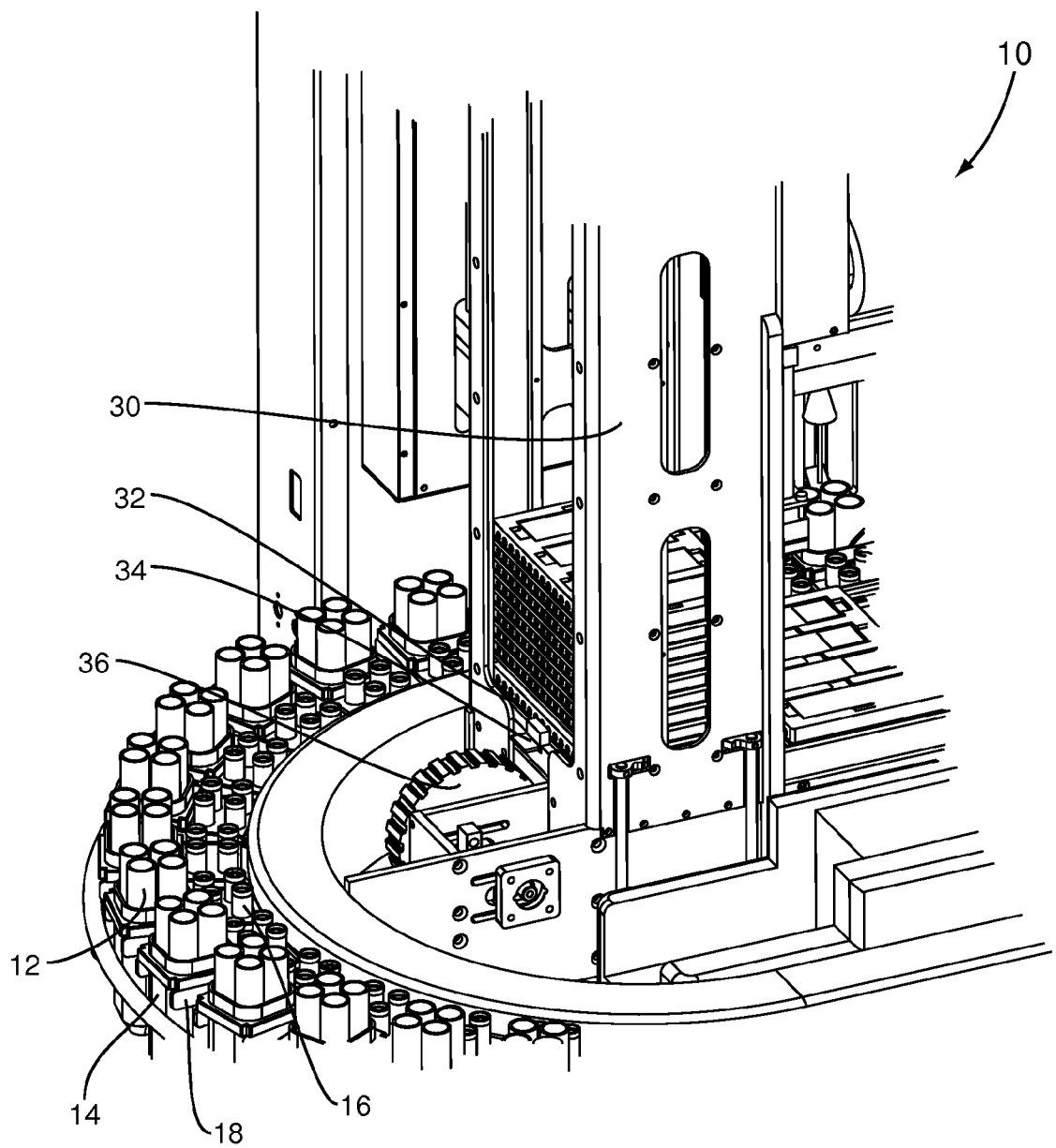
FIG. 5 illustrates exemplary tube racks with sample tubes associated with transfer tubes within rack carriers and illustrates a close-up of a tray downstacker, according to an embodiment of the subject matter described herein.

FIG. 5 illustrates the exemplary tube racks 14 with the sample tubes 12 associated with the transfer tubes 16 within the rack carriers 18 and illustrates a close-up of the tray downstacker 30. The belt 34 is illustrated to be in contact with the bottom tray 32 within the downstacker 30, but as described above, is not illustrated in its entirety to show details of the gear 36 which drives the belt 34. As described above, the belt 34 removes one tray 32 at a time from the tray downstacker 30 and moves that tray 32 forward for sample preparation.

Figure 6:
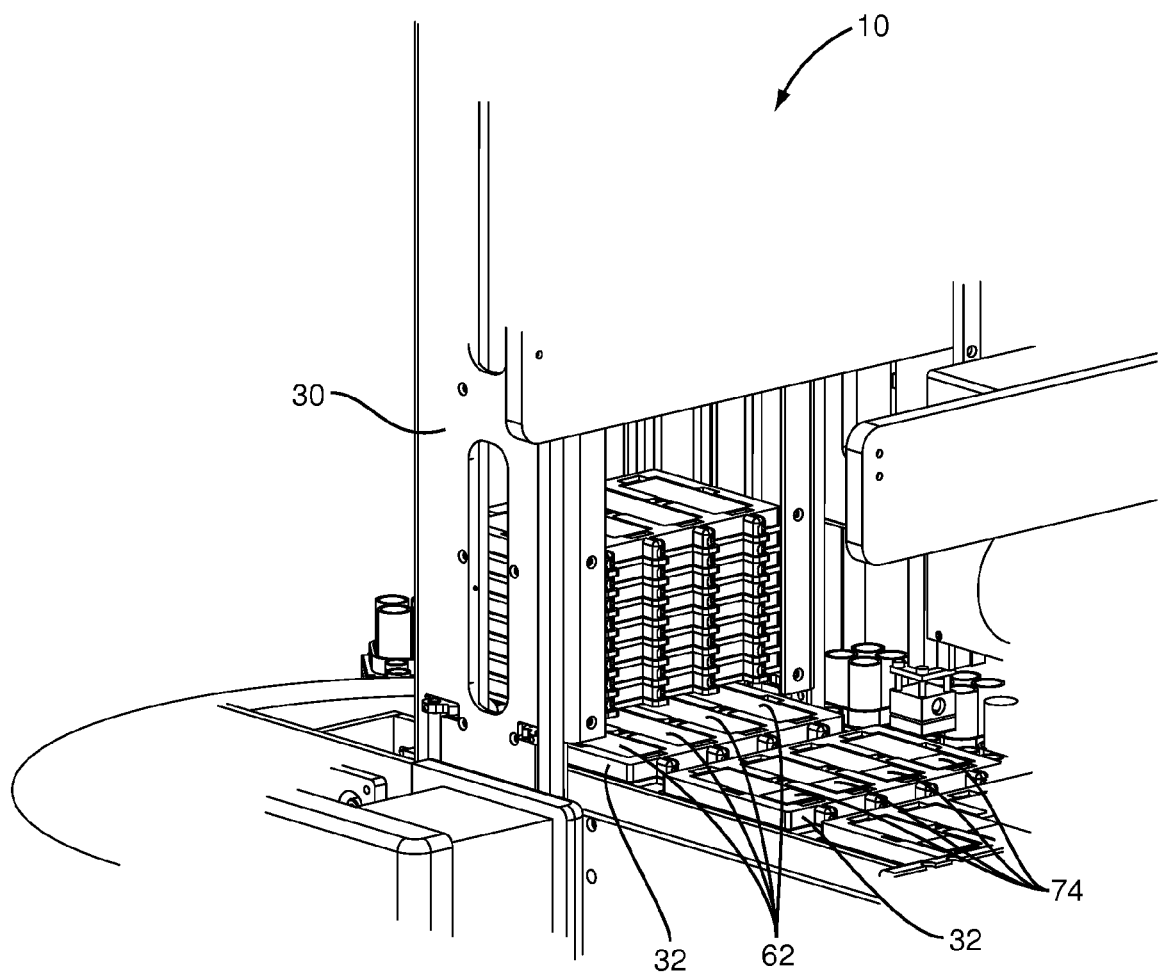
FIG. 6 illustrates an exemplary tray from a downstacker for slide sample preparation, according to an embodiment of the subject matter described herein.

FIG. 6 illustrates an exemplary tray 32 exiting from the tray downstacker 30 for slide sample preparation. The glass slides 62 are already located on the tray 32. However, the other tray 32, which has already advanced into the slide preparation area, has slide labels 74 already placed on the glass slides 62. Details of both label marking and placement will begin below in conjunction with FIG. 8A.

Figure 7:
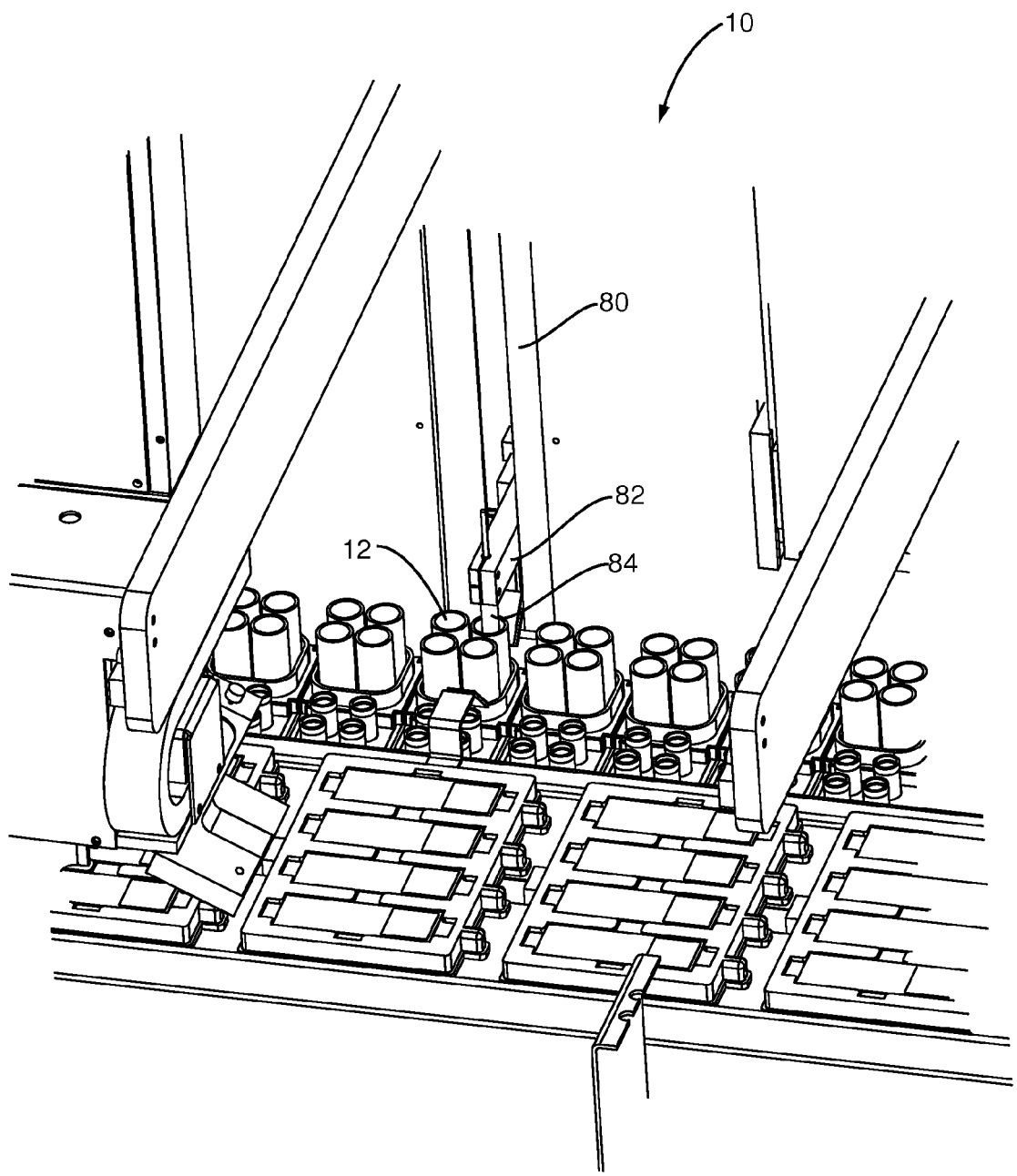
FIG. 7 illustrates an exemplary cell pellet measurement robotic arm that is used in conjunction with a cell pellet measurement end effector to measure a cell pellet within sample tubes, according to an embodiment of the subject matter described herein.

FIG. 7 illustrates an exemplary cell pellet measurement robotic arm 80 that is used in conjunction with a cell pellet measurement end effector 82 to measure the cell pellet 60 within the sample tubes 12. The cell pellet measurement robotic arm 80 is a two-axis robotic arm and is the third of four robotic arms used within the system 10. An exemplary ultrasonic level detection probe 84, which is used to measure the cell pellet 60 to determine a quantitative estimate of the cellularity of the cell pellet 60 within the sample tube 12, is also illustrated. As described above, photometric sensing or other sensing may be used to perform the quantitative estimate of the cellularity of the cell pellet 60 within the sample tube 12.

Exemplary algorithms that may be used at each stage of variable dilution of the cells within the cell pellet 60 will now be described. However, it is understood that many possible algorithms for the multiple differential dilutions of the cells within the cell pellet 60 described herein are possible. Accordingly, all possible algorithms are considered within the scope of the subject matter described herein.

As an example of an algorithm that may be used by the touch-screen monitor and control system 58 for the various differential dilutions described herein, the following exemplary slope-intercept equation (1) may be used.

$$\text{Dilution/Transfer Volume} = (\text{Detected Volume} * \text{Slope}) + \text{Offset} \quad (1)$$

This equation (1) may be used to determine the differential volume actions which are performed. The differential volume actions are the variable diluent addition to the sample tube 12, the optional variable cell adherent addition to the transfer tube 16, the variable transfer of the cell suspension from the sample tube 12 to the transfer tube 16, and the variable cell suspension or cell mixture (if adherent is mixed with the cell suspension) transfer volume to the glass slide 62 for thin-layer patterned cell sample preparation.

Exemplary offsets and slope values are represented within Equations (2) through (5) below.

$$\text{Diluent Volume} = (\text{Detected Volume} * 5 \text{ ul}) + 100 \text{ ul} \quad (2)$$

$$\text{Cell Adherent Volume} = (\text{Detected Volume} * 2 \text{ ul}) + 200 \text{ ul} \quad (3)$$

$$\text{Cell Suspension Transfer Volume} = (\text{Detected Volume} * 0) + 75 \text{ ul} \quad (4)$$

$$\text{Cell Mixture Volume} = (\text{Detected Volume} * 0) + 60 \text{ ul} \quad (5)$$

Within this exemplary embodiment, the ultrasonic level detection probe 84 is calibrated by measuring a distance from the tip of the ultrasonic level detection probe 84 to the bottom of an empty sample tube 12. This calibration distance may be used as a reference for determining the cellularity of the cell pellet 60 within the sample tube 12. During cell sample processing, the ultrasonic level detection probe 84 measures a distance from the tip of the ultrasonic level detection probe 84 to the top of the cell pellet 60. This distance is subtracted from the calibration distance to determine an elevation or height of the cell pellet 60. The height of the cell pellet 60 is used as a look-up entry for a look-up table. The look-up table stores volumetric values empirically derived to consider the rounded, conical shape near the bottom, and cylindrical upper portion of the sample tube 12. These volumetric values may be returned from a look-up operation on the look-up table and used within the respective equations (1) through (5) for differential volume processing as the volume (i.e., the Detected Volume), which represents the cellularity of the cell pellet 60.

An exemplary table may include entries for every 10 microliters (ul). Alternatively, entries within the table for every 100 ul, or any other usable granularity, may be used. The following exemplary Table (A) includes exemplary entries for 100 ul intervals. Interpolation of the values returned from the Table (A) may be used to provide increased granularity of the cellularity estimate (i.e., the Detected Volume within Equations (1) through (5)).

TABLE (A)

Exemplary Cellularity Volume Values

| Elevation Millimeters | Volume Microliters |
|---|---|
| 0 | 0 |
| 3.639 | 100 |
| 6.119 | 200 |
| 8.186 | 300 |
| 10.218 | 400 |
| 11.79 | 500 |
| 13.068 | 600 |
| 14.041 | 700 |

Figure 8A:
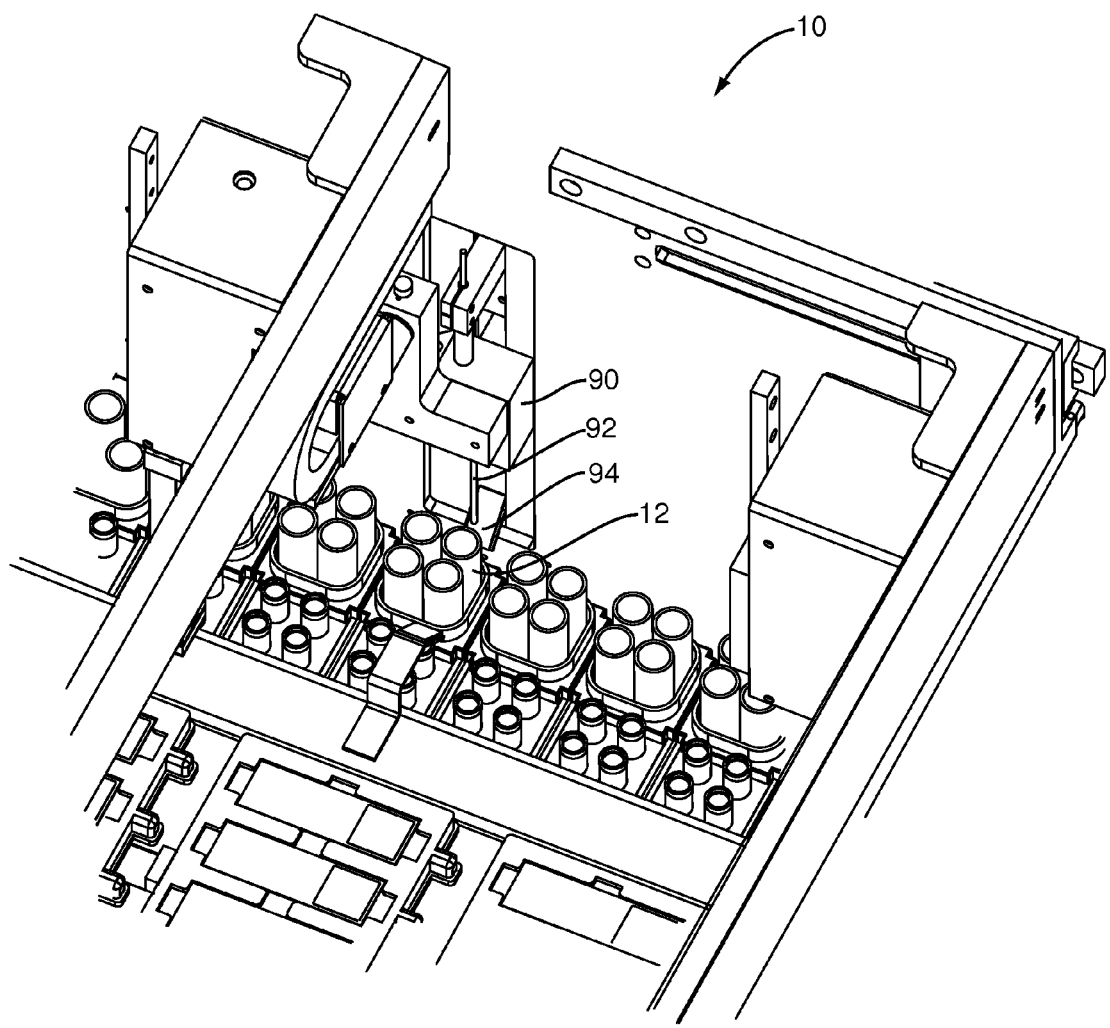
FIG. 8A illustrates an exemplary barcode reader projecting a beam onto a mirror to read a label on the side of a sample tube, according to an embodiment of the subject matter described herein.

FIG. 8A begins the description of sample tracking. An exemplary barcode reader 90 is illustrated projecting a beam 92 onto a rear barcode reader mirror 94 to read tracking information (not shown) from the side of the sample tube 12. As will be described in more detail below, exemplary tracking information may be in the form of a barcode printed on a label affixed to the side of the sample tube 12. The tracking information retrieved from the sample tube 12 may be used for tracking purposes and label printing for the slide label 74, which is placed upon the glass slide 62, and may be associated with the prepared sample derived from the sample tube 12.

Figure 8B:
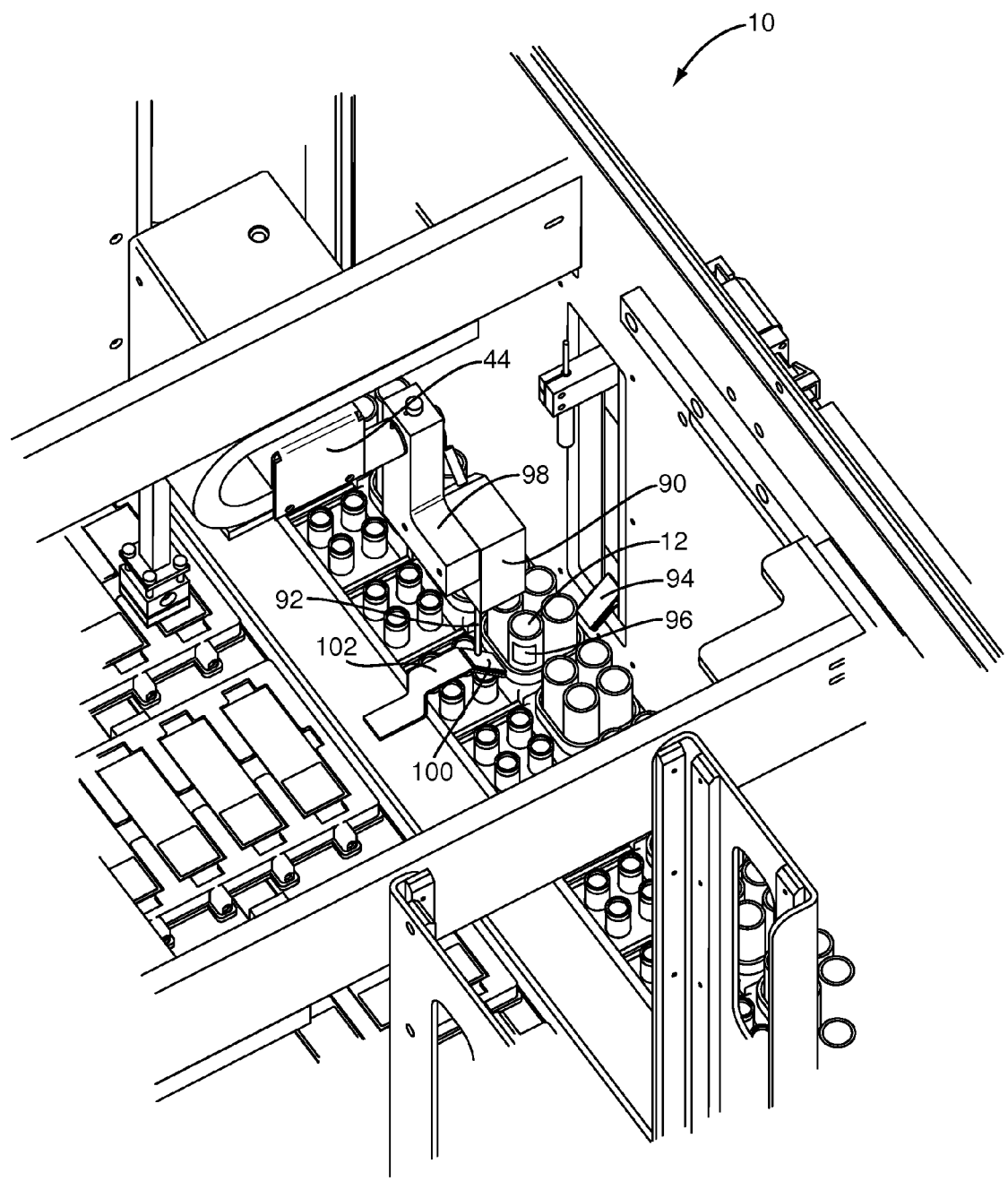
FIG. 8B illustrates an exemplary barcode reader reading a label from a sample tube positioned opposite a sample tube described in association with FIG. 8A, according to an embodiment of the subject matter described herein.

FIG. 8B illustrates the exemplary barcode reader 90 reading a tube label 96 from a sample tube 12 positioned opposite the sample tube 12 described above in association with FIG. 8A. The barcode reader 90 is attached to a barcode reader arm 98 and has been moved from its position illustrated in FIG. 8A above the rear barcode reader mirror 94 to a position above a front barcode reader mirror 100 to read the tube label 96. The front barcode reader mirror 100 is supported on a bracket 102 and the barcode reader arm 98 is shown to be mounted to the label end effector 44. The position of the barcode reader arm 98 is additionally controlled by movement of the label end effector 44. The information retrieved from the tube label 96 may be used to print the slide label 74, as described in more detail below.

Figure 9:
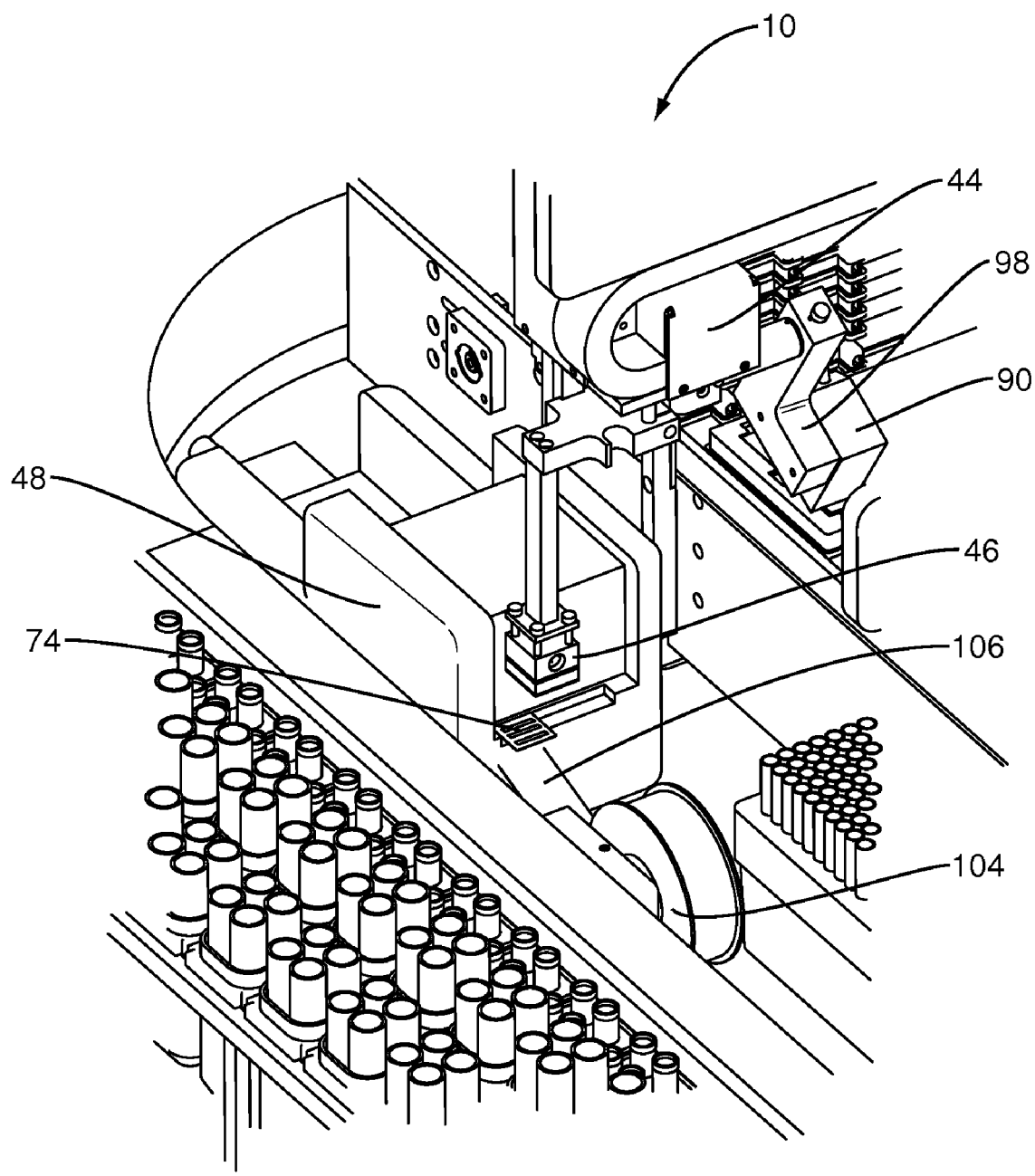
FIG. 9 illustrates an exemplary label printer for printing, according to an embodiment of the subject matter described herein.

FIG. 9 illustrates an exemplary label printer 48 dispensing a printed slide label 74. A backing re-wind roll 104 includes a label backing material 106 wound upon it. The vacuum foot 46 is shown to have been moved to a position just above the printed slide label 74 by the label end effector 44. Additionally, FIG. 9 also illustrates that the barcode reader arm 98 has been retracted and that the barcode reader 90 is no longer in a position to read a tube label 96 from the sample tube 12 via the front barcode reader mirror 100.

Figure 10:
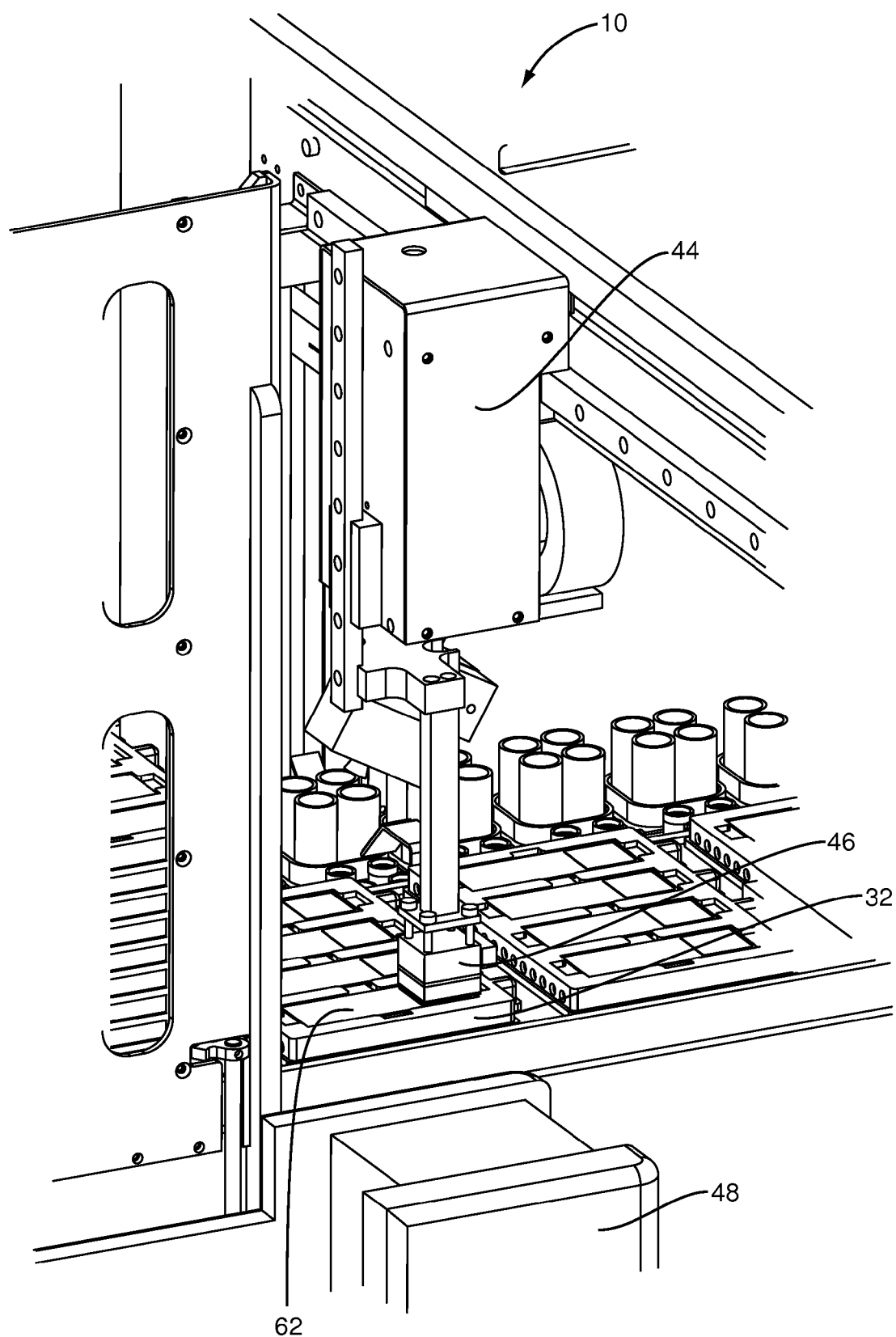
FIG. 10 illustrates an exemplary vacuum foot placing a label on a first slide on a tray, according to an embodiment of the subject matter described herein.

FIG. 10 illustrates the exemplary vacuum foot 46 placing the slide label 74 on the first glass slide 62 on the tray 32. The label end effector 44 has been moved from a location above the label printer 48 to a location above the first glass slide 62 within the tray 32. As additional tube labels 96 are scanned from the sample tubes 12 using the barcode reader 90, new slide labels 74 are printed. The label end effector 44 will move horizontally between a position above either the rear barcode reader mirror 94, the front barcode reader mirror 100, or the label printer 48 to scan and print barcodes on the slide labels 74 and to allow the vacuum foot 46 to retrieve a new slide label 74. After retrieval of each slide label 74, the label end effector 44 will move to a position above the appropriate glass slide 62 for placement of the slide label 74 onto the glass slide 62.

Figure 11:
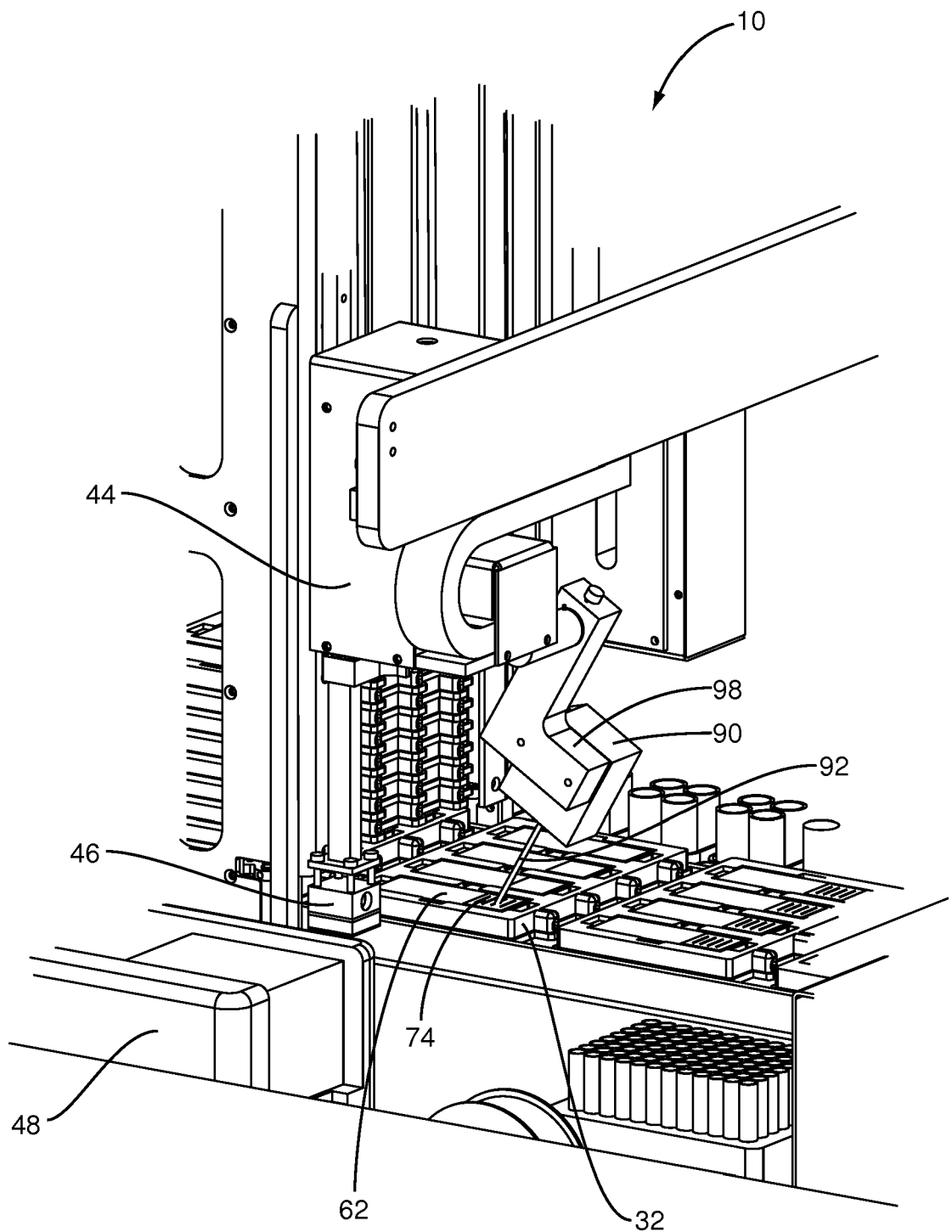
FIG. 11 illustrates an exemplary barcode reader scanning a label on a first slide within a tray after placement, according to an embodiment of the subject matter described herein.

FIG. 11 illustrates the exemplary barcode reader 90 scanning the slide label 74 on the first glass slide 62 within the tray 32 after placement. The barcode reader arm 98 is rotated to a position which allows the barcode reader 90 to read the code placed on the slide label 74 without use of a mirror. Additionally, as described above, the barcode reader arm 98 is connected to the label end effector 44 and moves relative to the label end effector 44 and the vacuum foot 46. As such, it should be noted that each slide label 74 may be scanned for accuracy in conjunction with retrieval of the next slide label 74 from the label printer 48 by the vacuum foot 46.

Figure 12:
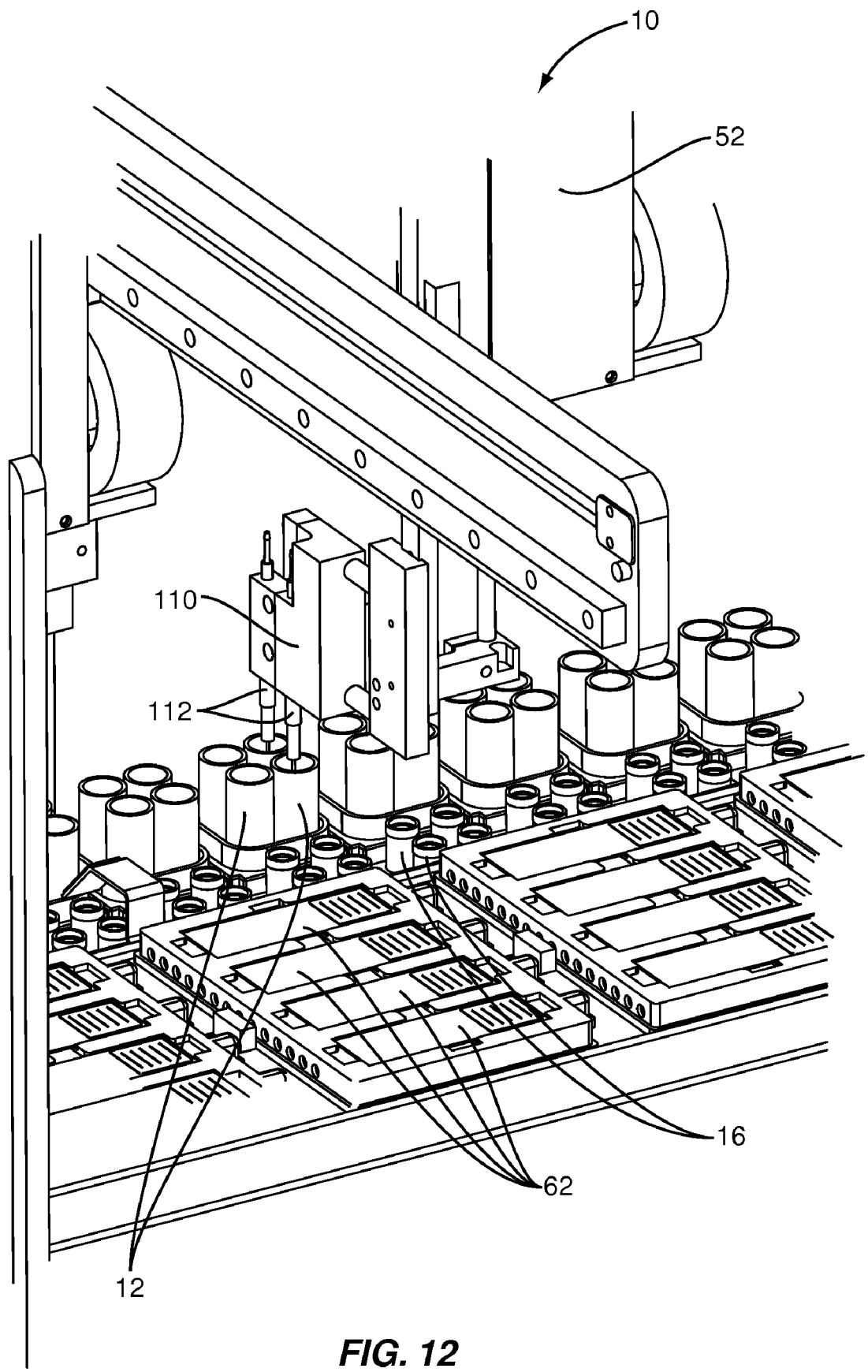
FIG. 12 illustrates an exemplary thin-layer cell sample slide preparation system dispensing a differential volume of diluent into two sample tubes, according to an embodiment of the subject matter described herein.

FIG. 12 illustrates the exemplary system 10 dispensing a differential volume of diluent into a sample tube 12. Two fluid probes 112 are illustrated within FIG. 12. The front fluid probe 112 (e.g., closest to the glass slides 62) is used to dispense diluent to the sample tubes 12 which are currently being processed. The back fluid probe 112 (e.g., furthest from the glass slides 62) can also dispense cell adherent to the transfer tubes 16, as will be described in more detail beginning with FIG. 13 below.

Regarding dispensing of the diluent to the sample tubes 12 within the exemplary embodiment described herein, the front fluid probe 112 dispenses a differential volume of diluent to one of the sample tubes 12 and then is moved to dispense diluent to the other sample tube 12. For example, the front fluid probe 112 may be positioned by the fluid handling end effector 52 to dispense diluent into the front sample tube 12 (e.g., closest to the glass slides 62) and may then be moved by the fluid handling end effector 52 to dispense diluent into the back sample tube 12 (e.g., furthest from the glass slides 62). However, this order may be changed and the dispensing of diluent to the two sample tubes 12 may be performed in any order without departure from the scope of the subject matter described herein. Additionally, either fluid probe 112 may be used to dispense diluent with the other fluid probe 112 that may be used to dispense cell adherent without departure from the scope of the subject matter described herein. Accordingly, any such combination of dispensing order or fluid probe 112 assignment is considered within the scope of the subject matter described herein.

As described above, the differential volume dispensed to each of the two sample tubes 12 being processed is selected based upon the estimated cellularity of the respective cell pellet 60 within each of the sample tubes 12. A fluid probe arm 110 is illustrated above the two sample tubes 12 placing the fluid probes 112 above the sample tubes 12 in a position for dispensing diluent into the front sample tube 12. As described above, the diluent may be water, saline, buffered saline, or a similar substance. It should be noted that the fluid probe arm 110 is used in conjunction with the syringe pump 54 and the switch 56 to control the dispensing of diluent and cell adhesive to the sample tubes 12 and the transfer tubes 16, respectively. Additionally, the syringe pump 54 and the switch 56 are used for aspiration of the cell suspension from the sample tubes 12, for dispensing the cell suspension into the transfer tubes 16, and for aspiration of the resulting cell mixture from the transfer tubes 16 directly onto the glass slides 62 to prepare the sample, as will be described in more detail below.

Figure 13:
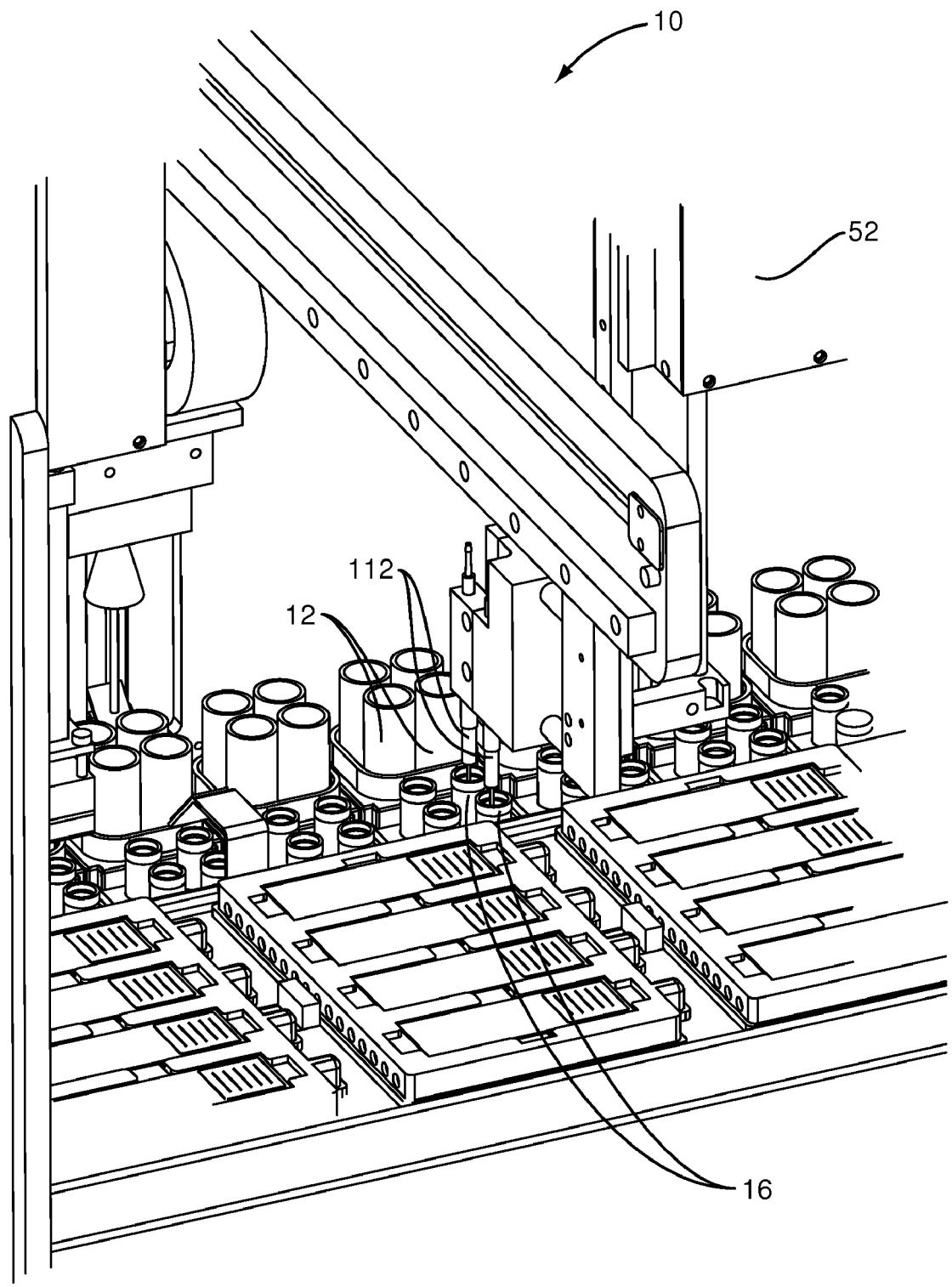
FIG. 13 illustrates that an exemplary fluid handling end effector has been moved to position two fluid probes over two transfer tubes associated with two sample tubes which are currently being processed, according to an embodiment of the subject matter described herein.

FIG. 13 illustrates that the exemplary fluid handling end effector 52 has been moved to position the two fluid probes 112 over two of the transfer tubes 16 which are associated with the two sample tubes 12 which are currently being processed. As described above, within the exemplary embodiment described herein, the front fluid probe 112 dispenses diluent and if an adherent is mixed with the cell suspension, the back fluid probe 112 can dispense cell adherent. FIG. 13 illustrates the alignment used to dispense cell adherent to the back transfer tube 16 (e.g., closest to the sample tubes 12). The fluid handling end effector 52 is then moved forward to align the back fluid probe 112 with the front transfer tube 16 (e.g., furthest from the sample tubes 12) for dispensing cell adherent to the front transfer tube 16. As with the differential volume of diluent dispensed into each sample tube 12 based upon the cellularity estimate of the cell pellet 60 within each sample tube 12, a differential volume of cell adherent can be dispensed into each of the associated transfer tubes 16 based upon the unique estimate of cellularity within each associated sample tube 12. Accordingly, as described above, the cell pellet 60 within each of the sample tubes 12 in this embodiment has been variably diluted and the transfer tubes 16 have had a variable volume of cell adherent dispensed into them based upon the cellularity estimate of the cell pellet 60 within the respective sample tube 12.

Figure 14:
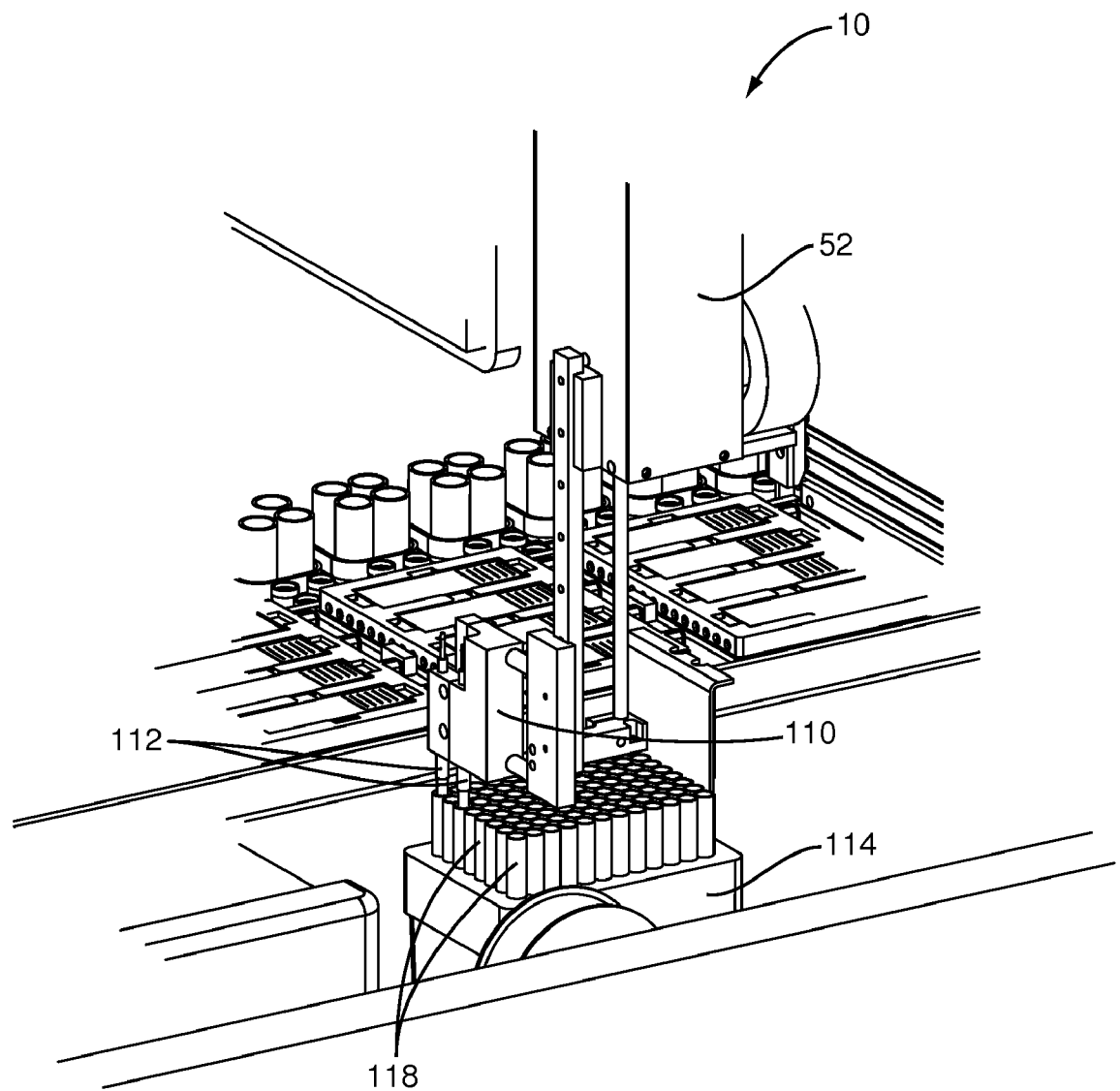
FIG. 14 illustrates that an exemplary fluid handling end effector has been moved to place a fluid probe arm above a pipette tip rack that includes disposable pipette tips, according to an embodiment of the subject matter described herein.

FIG. 14 illustrates that the exemplary fluid handling end effector 52 has been moved to place the fluid probe arm 110 above a pipette tip rack 114 that includes disposable pipette tips 118. The fluid probe arm 110 is positioned such that the two fluid probes 112 are pressed into two of the disposable pipette tips 118 to retrieve the two disposable pipette tips 118 to further process the cell samples.

Figure 15:
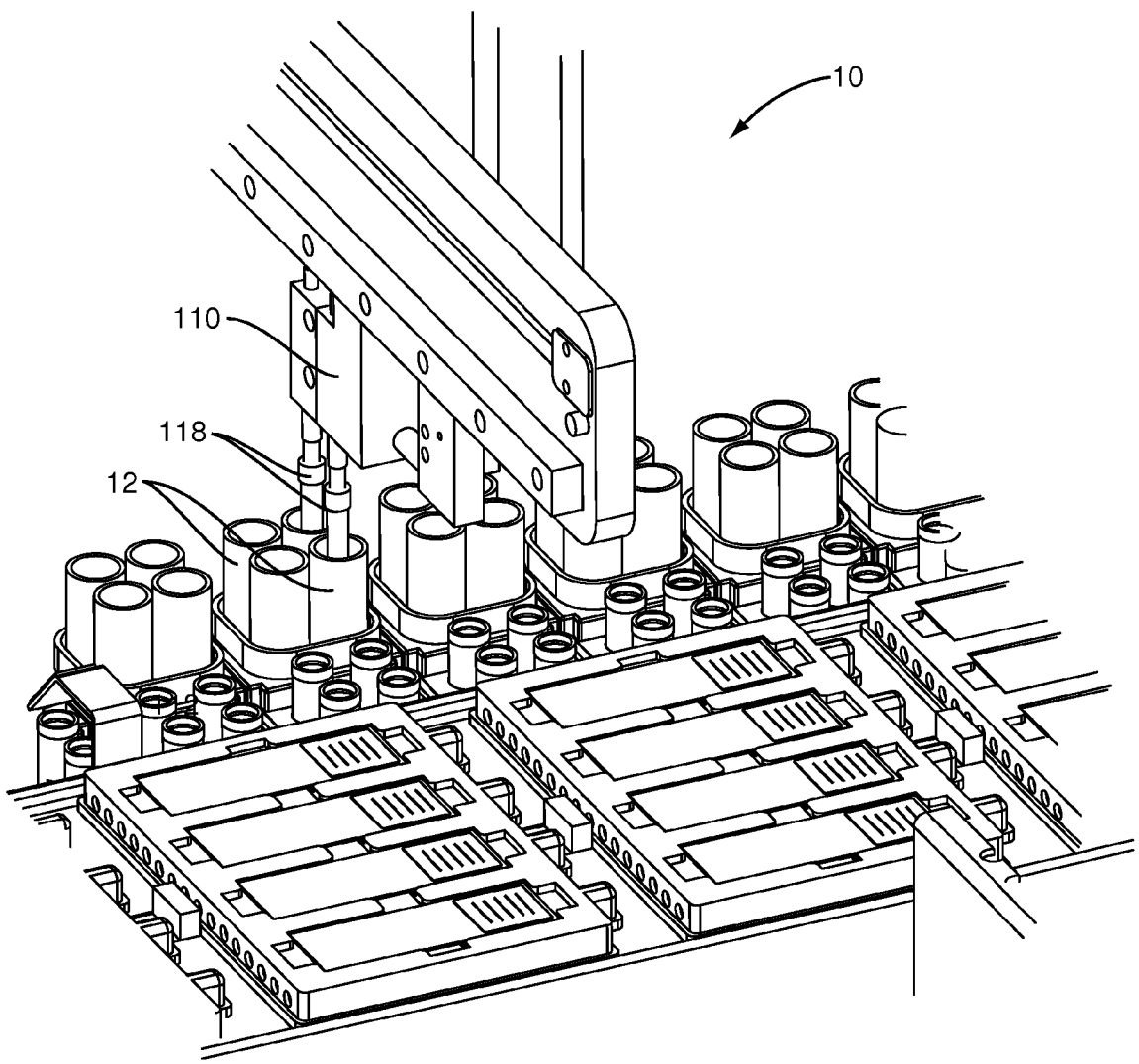
FIG. 15 illustrates that an exemplary fluid probe arm has been repositioned via a fluid handing end effector to aspirate a differential volume from sample tubes which are currently being processed by use of disposable pipette tips, according to an embodiment of the subject matter described herein.

FIG. 15 illustrates that the exemplary fluid probe arm 110 has been repositioned via the fluid handing end effector 52 (not shown) to aspirate a differential volume from each of the sample tubes 12 by use of the disposable pipette tips 118. As described above, based upon the cellularity estimate of each cell pellet 60 within the respective sample tubes 12, a different volume of the cell suspension will be aspirated from each sample tube 12.

Figure 16:
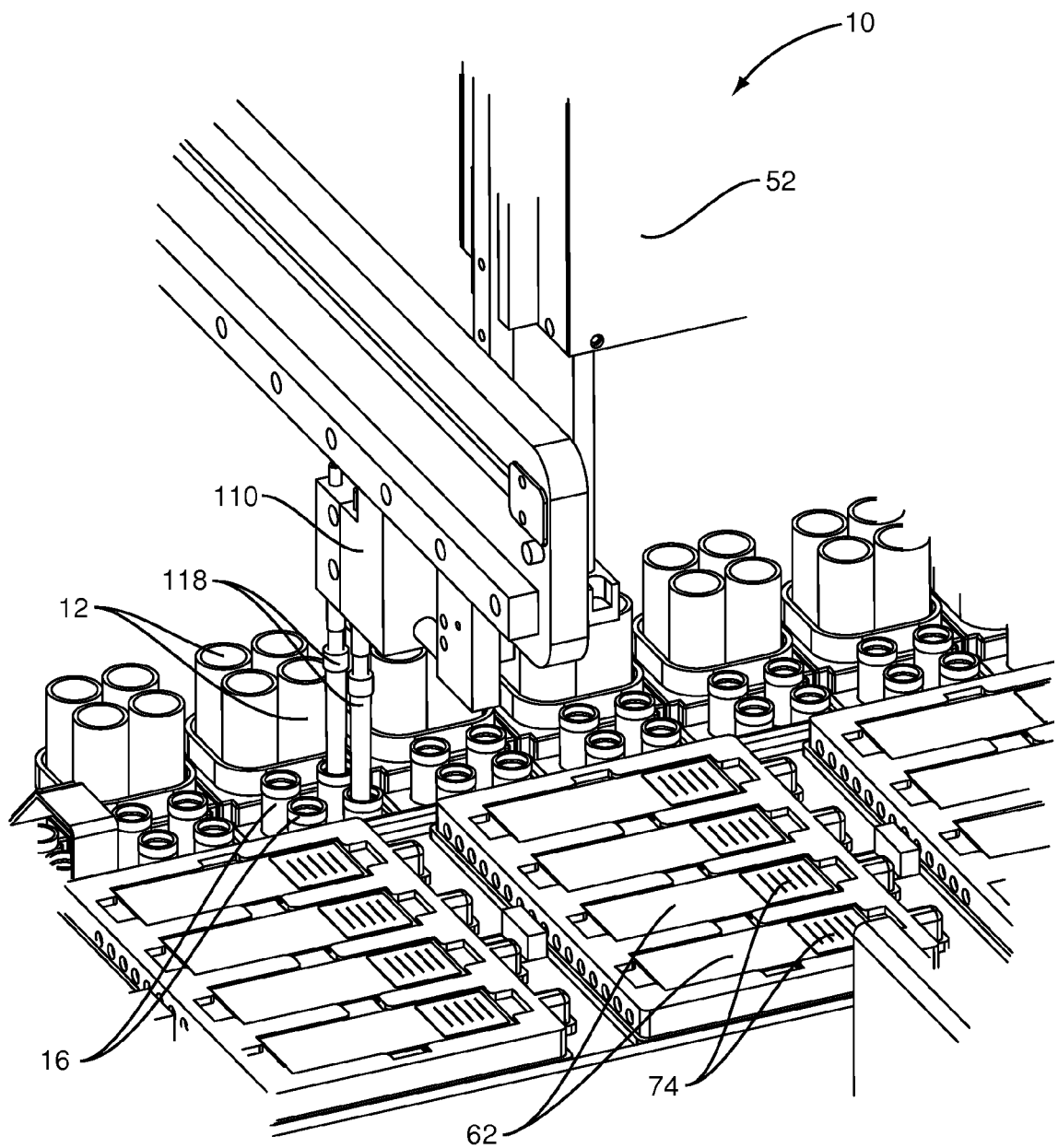
FIG. 16 illustrates that an exemplary fluid probe arm is positioned above two transfer tubes which are associated with current sample tubes being processed to dispense a differential volume of cell suspension into a respective transfer tube and to aspirate a resulting cell mixture from a respective transfer tube for correct placement onto associated slides to create a thin-layer cell sample, according to an embodiment of the subject matter described herein.

FIG. 16 illustrates that the exemplary fluid probe arm 110 is positioned above the two transfer tubes 16 associated with the two sample tubes 12 and the aspirated cell suspension from each sample tube 12 is dispensed into the respective transfer tube 16 and aspirated for patterned placement onto associated glass slides 62. The disposable pipette tips 118 are associated with the current sample tubes 12 being processed to dispense a differential volume of cell suspension into the respective transfer tube 16. After dispensing the differential volume of the cell suspension to the respective transfer tube 16, the resulting cell mixture is aspirated from the respective transfer tube 16 for correct placement onto the associated glass slides 62 to create a thin-layer cell sample.

Figure 17:
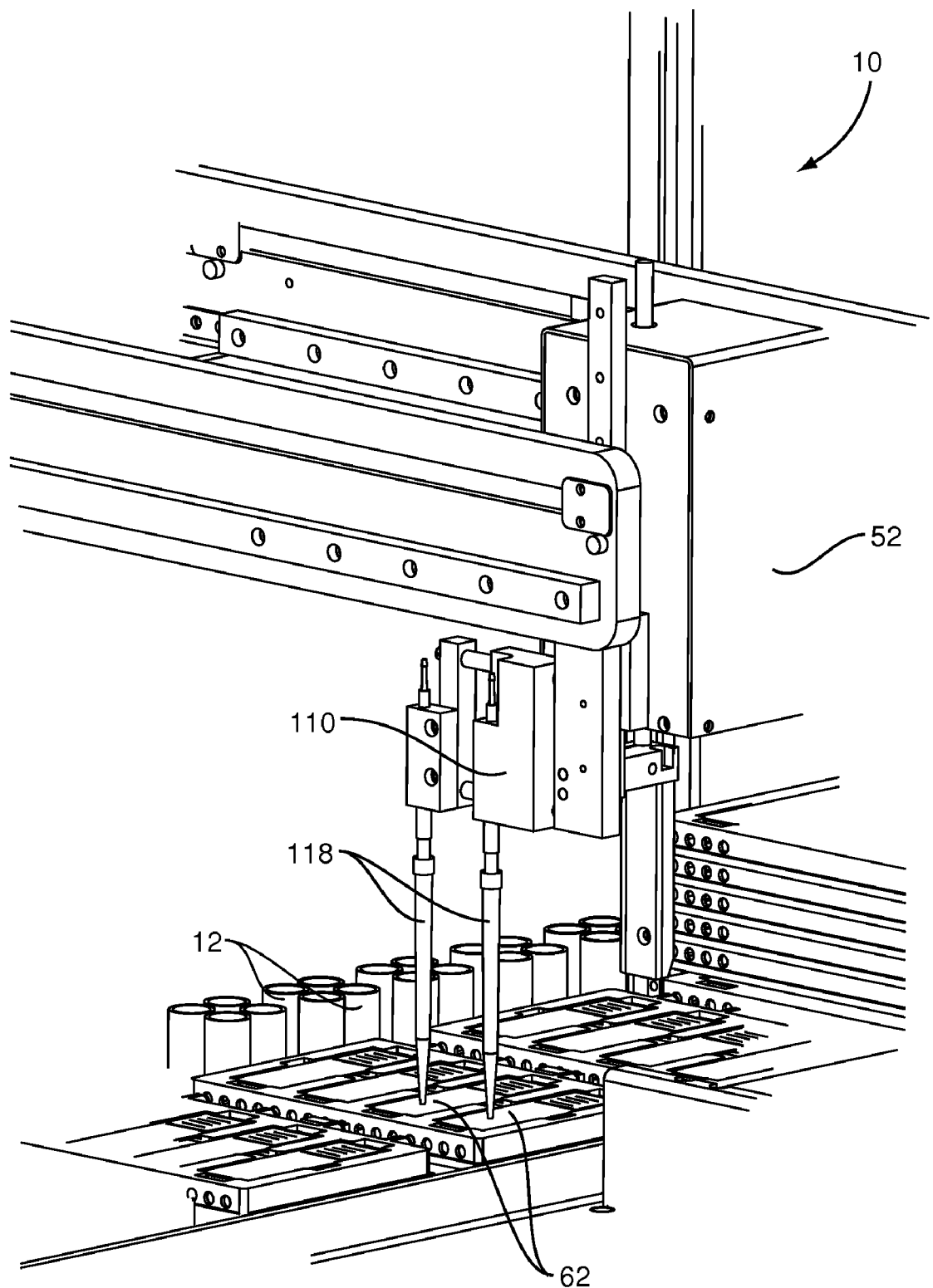
FIG. 17 illustrates an exemplary thin-layer cell sample slide preparation system dispensing a thin-layer cell sample in a pattern directly onto slides which are associated with current cell samples within sample tubes, according to an embodiment of the subject matter described herein.

FIG. 17 illustrates the exemplary system 10 dispensing a thin-layer cell sample in a pattern directly onto the glass slides 62 which are associated with the current cell samples within the sample tubes 12. The fluid handling robotic arm 50 has been moved via the fluid handling end effector 52 such that the disposable pipette tips 118 are slightly above and in close proximity to the glass slides 62 which are associated with the cell samples. The fluid handling end effector 52 is then moved to pattern dispense the prepared cell mixture to form a thin-layer cell sample into a pattern selectable by the user. As described above sample tracking is provided throughout the processing of the system 10 via the slide labels 74. Alternatively, another barcode reader may be placed on the fluid handling robotic arm 50 to provide additional tracking capabilities by re-scanning the slide label 74 on the glass slide 62 when the cell mixture is pattern dispensed to the glass slides 62.

Figure 18A:
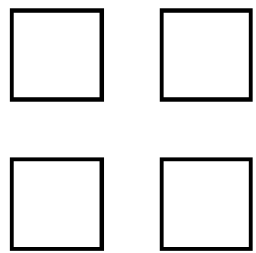
FIG. 18A illustrates an exemplary repeated square pattern that may be used to dispense a cell mixture into four square-patterned samples on a surface of a slide for analysis, according to an embodiment of the subject matter described herein.

FIGS. 18A-18D illustrate exemplary dispensing patterns that may be used to dispense the cell mixture to the glass slides 62 in a pattern selected by the user. By allowing pattern selection for cell mixture dispensing, the user may be better able to analyze the resulting prepared samples. FIG. 18A illustrates an exemplary repeated square pattern that may be used to dispense the cell mixture into four square-patterned samples on the surface of the glass slide 62 for analysis. The squares represent the boundary of the cell pattern with the interior of each square filled with a thin layer of cells. Alternatively, the boundary may be dispensed without filling the interior of each square, as desired.

Figure 18B:
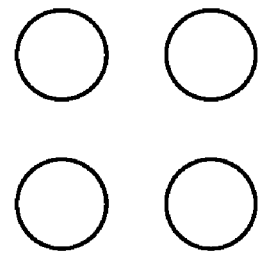
FIG. 18B illustrates an exemplary repeated circular pattern that may be used to dispense a cell mixture into four circular-patterned samples on a surface of a slide for analysis, according to an embodiment of the subject matter described herein.
Figure 18C:
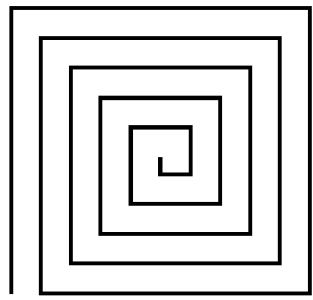
FIG. 18C illustrates an exemplary square spiral pattern that may be used to dispense a cell mixture into a square spiral-patterned sample on a surface of a slide for analysis, according to an embodiment of the subject matter described herein.
Figure 18D:
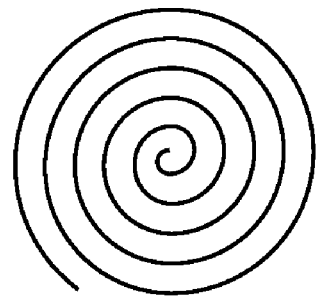
FIG. 18D illustrates an exemplary circular spiral pattern that may be used to dispense a cell mixture into a circular spiral-patterned sample on a surface of a slide for analysis, according to an embodiment of the subject matter described herein.

FIG. 18B illustrates an exemplary repeated circular pattern that may be used to dispense the cell mixture into four circular-patterned samples on the surface of the glass slide 62 for analysis. To achieve the square or circular pattern in FIGS. 18A and 18B with the interior of each square filled with a thin layer of cells, the robotic arm 50 dispenses fluid while tracing out a path. The path followed by the robotic arm 50 allows the fluid to fill in the area of the desired pattern. FIG. 18C illustrates an exemplary square spiral path that may be used to dispense the cell mixture into a square pattern sample on the surface of the glass slide 62 for analysis. FIG. 18D illustrates an exemplary circular spiral path that may be used to dispense the cell mixture into a circular pattern sample on the surface of the glass slide 62 for analysis. Rectangles or other geometric shapes are possible, including patterns such as discrete lines in which the cell mixture does not spread out to fill in the area of the pattern. Additionally, paths, such as the square spiral path and the circular spiral path described above, may be traversed on a larger grid to dispense discrete lines in which the cell mixture does not spread out to fill in an area. Many other combinations of paths and patterns are possible and all are considered within the scope of the subject matter described herein.

Figure 19A:
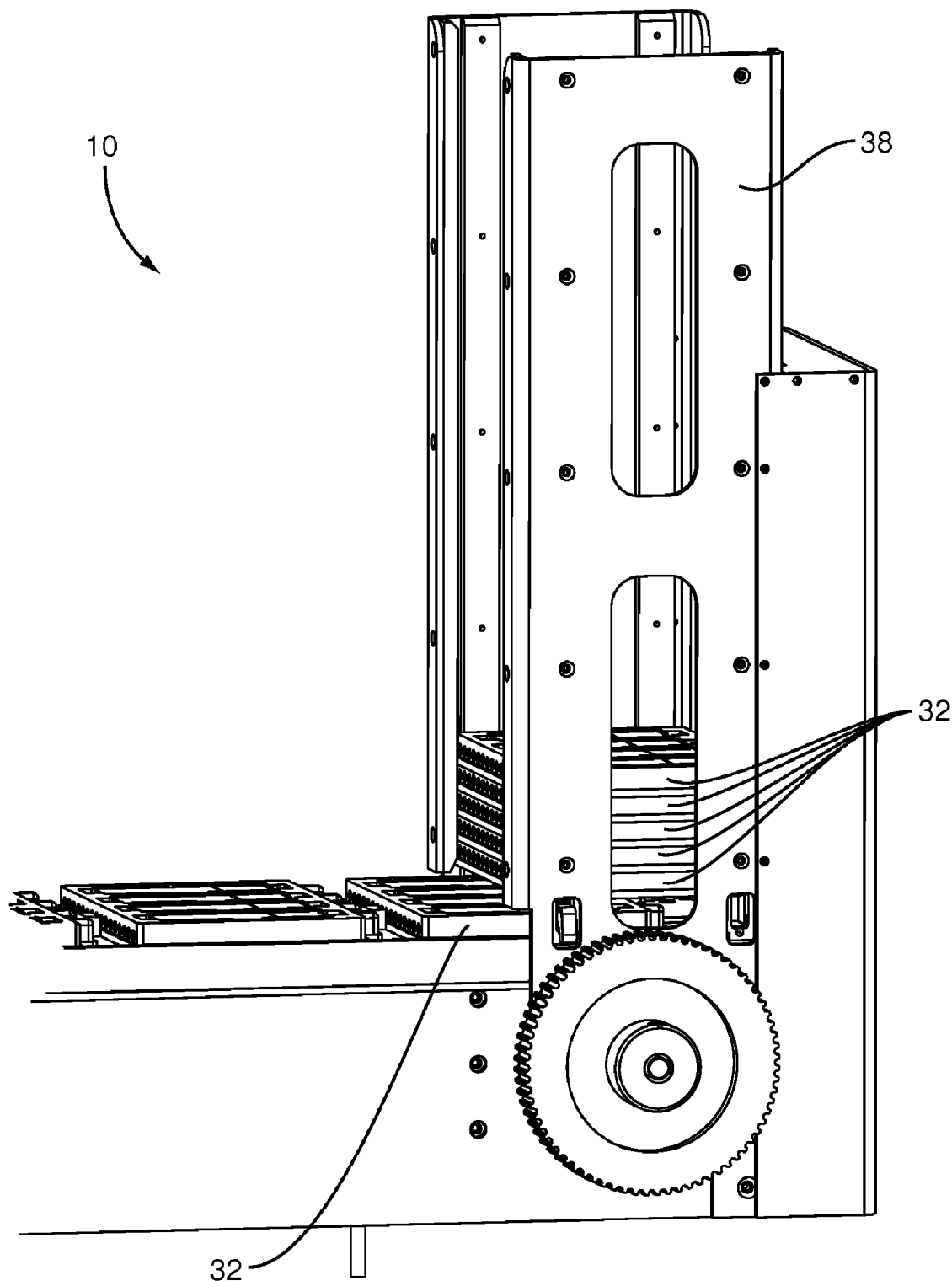
FIG. 19A illustrates an exemplary tray upstacker in more detail and shows a tray moving into the tray upstacker, according to an embodiment of the subject matter described herein.
Figure 19B:
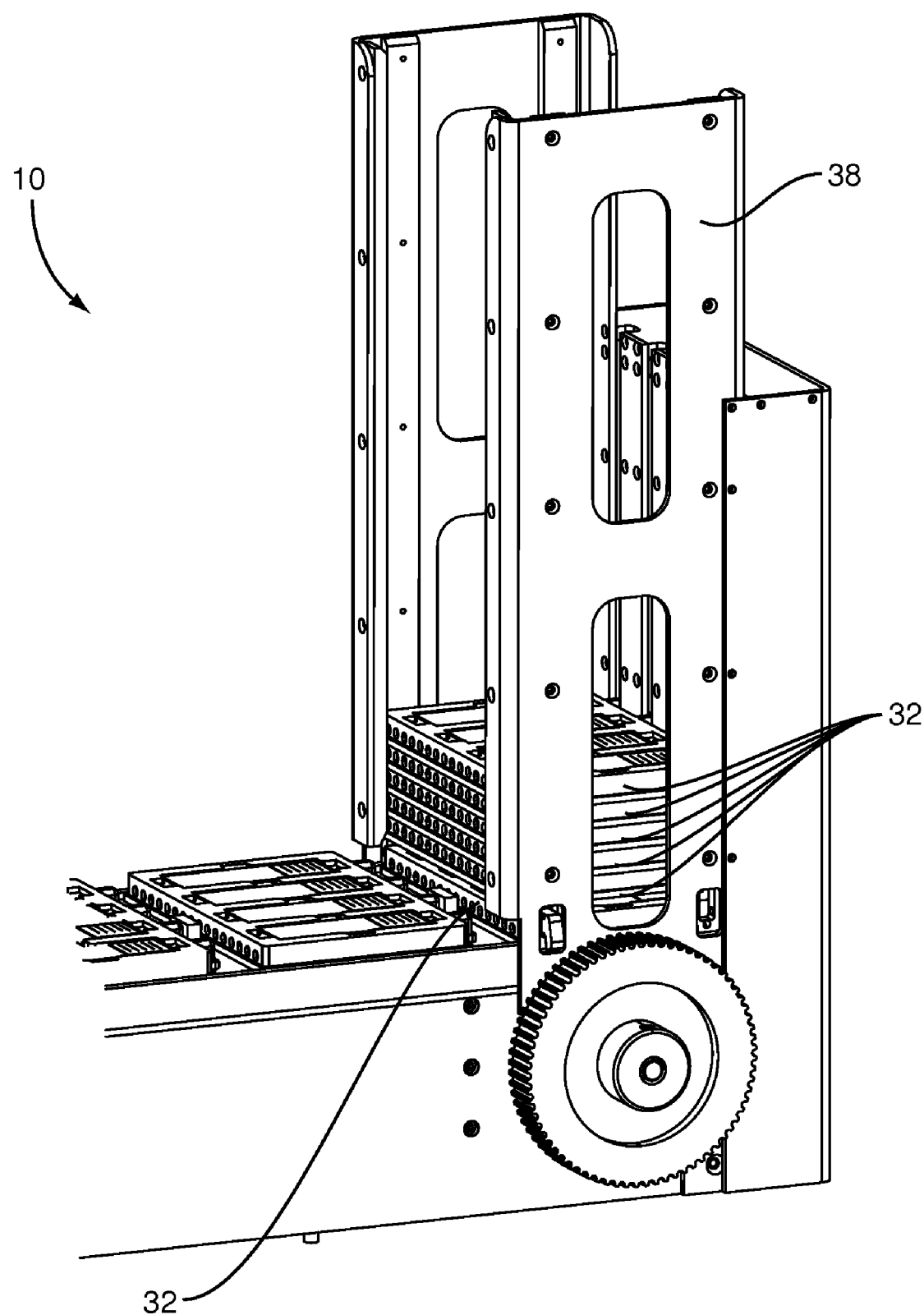
FIG. 19B illustrates an exemplary tray positioned in vertical alignment with a tray upstacker and ready to be lifted, according to an embodiment of the subject matter described herein.
Figure 20:
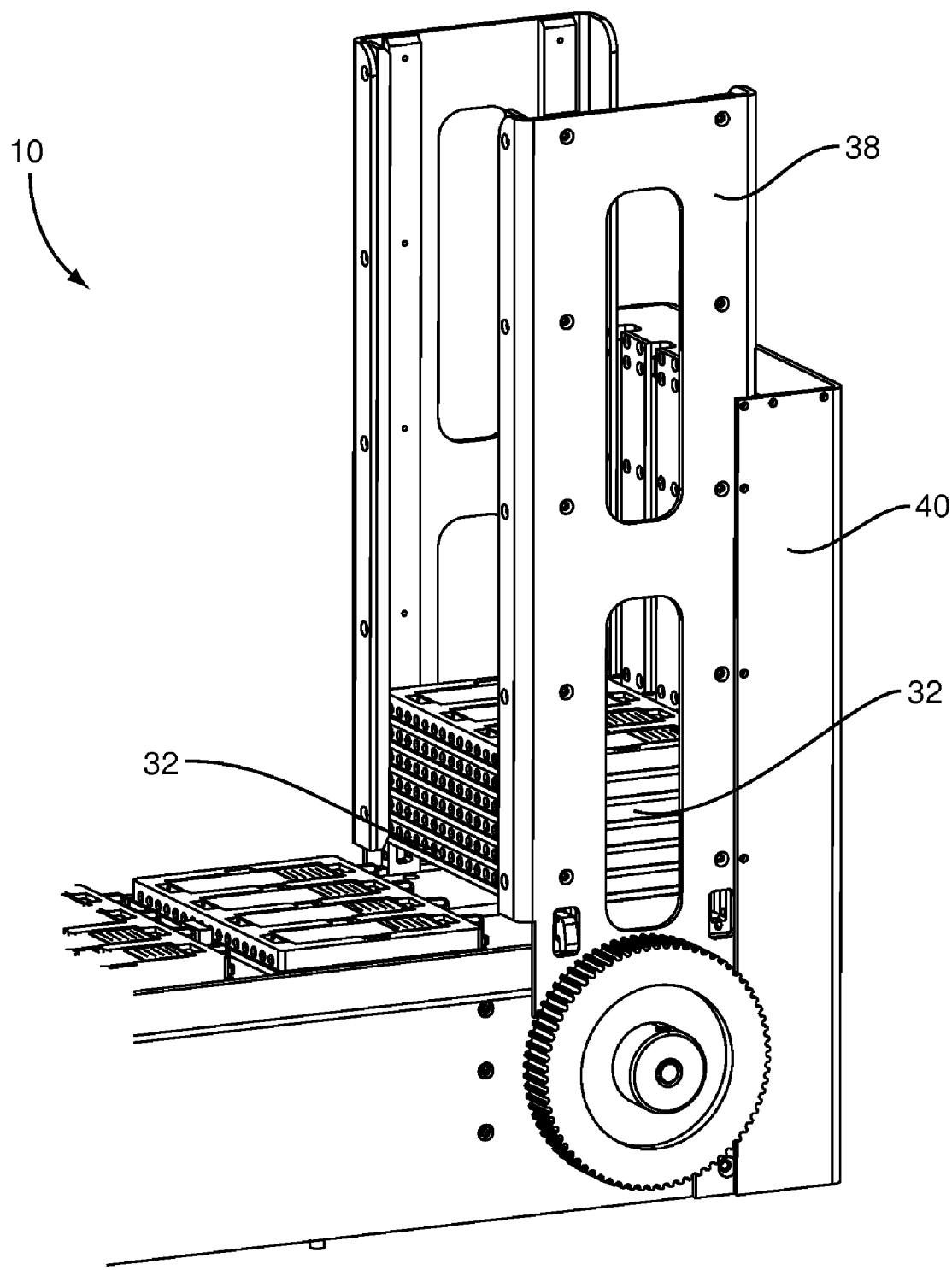
FIG. 20 illustrates an exemplary tray within a tray upstacker after it has been lifted, according to an embodiment of the subject matter described herein.

FIGS. 19A, 19B, and 20 illustrate the tray upstacker 38 in more detail. FIG. 19A illustrates a tray 32 moving into the tray upstacker 38. Additional trays 32 have already been lifted into the tray upstacker 38 for drying. FIG. 19B illustrates the tray 32 positioned in vertical alignment with the tray upstacker 38, ready to be lifted. FIG. 20 illustrates the tray 32 within the tray upstacker 38 after it has been lifted. As will be described below, the air discharge chamber 40 provides positive air pressure and air flow through the trays 32.

Figure 21:
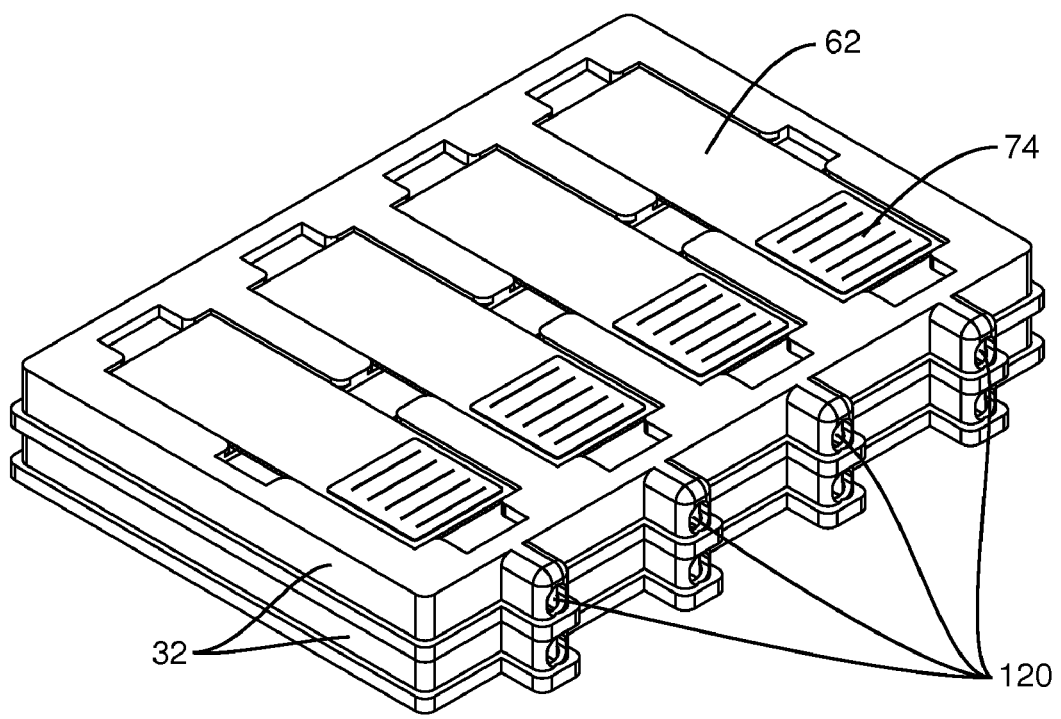
FIG. 21 illustrates two exemplary trays stacked with slides and labels and illustrates tray air inlet nozzles which are used to direct air from an air discharge chamber over a surface of the slides for drying, according to an embodiment of the subject matter described herein.

FIG. 21 illustrates two exemplary trays 32 stacked with glass slides 62, slide labels 74, and tray air inlet nozzles 120 which are used to direct air from the air discharge chamber 40 over the surface of the glass slides 62 for drying. The trays 32 stack and form a seal between the top of the bottom tray 32 and the bottom of the top tray 32. Accordingly, the tray air inlet nozzles 120 of the top tray 32 provide an air flow path across the corresponding glass slide 32 located on the bottom tray 32 (not shown). As each new tray 32 enters the tray upstacker 38, the tray 32 above it comes into contact with the tray 32 that has just entered the tray upstacker 38 and drying of the glass slides 62 on the lower tray 32 begins.

Figure 22:
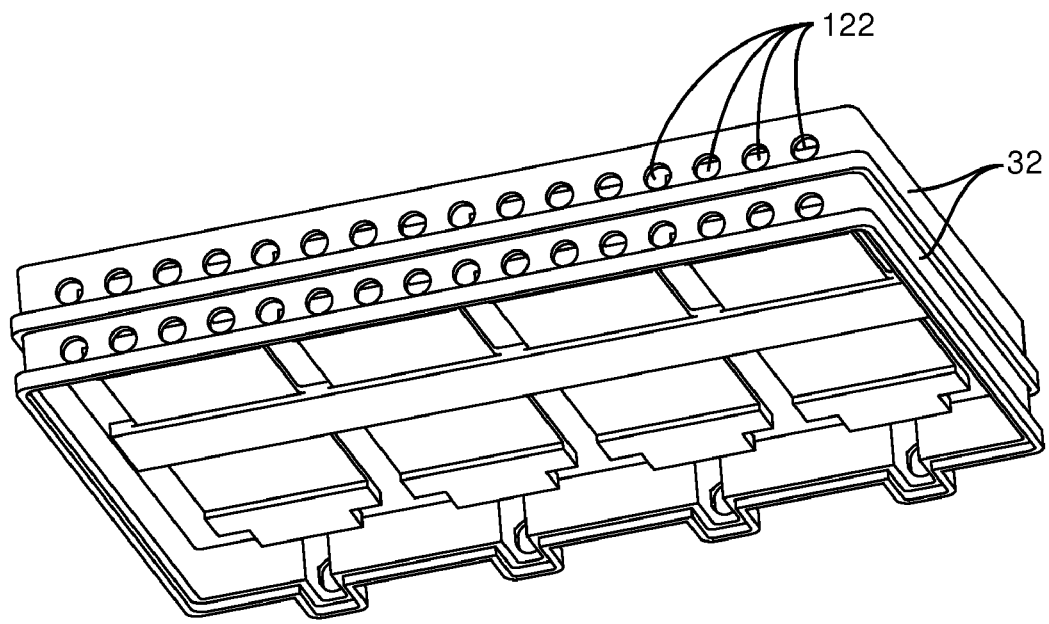
FIG. 22 illustrates two exemplary stacked trays from an air discharge side to show where air exits at a back edge of the trays to remove moisture from thin-layer cell samples, according to an embodiment of the subject matter described herein.

FIG. 22 illustrates two exemplary stacked trays 32 from the air discharge side to show air discharge holes 122 which allow air to exit at the back edge of the trays 32 to remove moisture from the thin-layer cell samples on the glass slides 62. The air discharge holes 122 are located across a back edge of each tray 32 to allow air, which is forced into the tray air inlet nozzles 120, to escape. It should be noted that the air discharge holes 122 are larger than the tray air inlet nozzles 120. However, many relationships between the air discharge holes 122 and the tray air inlet nozzles 120 is possible and all are considered within the scope of the subject matter described herein. Additionally, it should be noted that the air entering the air discharge chamber 40 may be treated to remove moisture from or to increase the temperature of the incoming air to facilitate more rapid drying of the thin-layer cell samples on the glass slides 62. Variations in the treatment of the incoming air may be optimized based upon conditions within the surrounding ambient air. For example, in a humid environment, de-humidifying the air prior to entry into the air discharge chamber 40 may accelerate drying.

Figure 23:
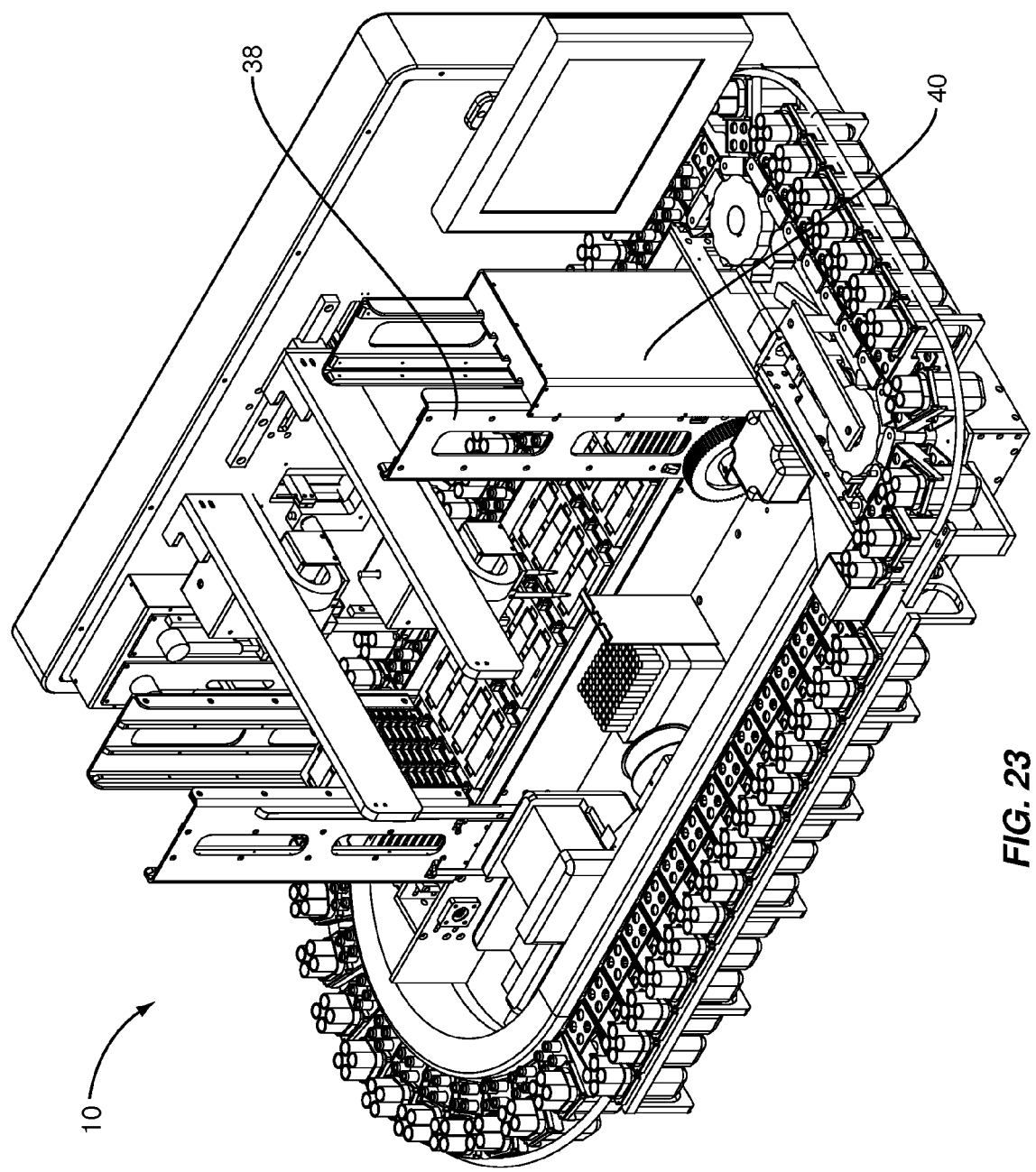
FIG. 23 illustrates an exemplary top right isometric view of an automated continuous multi-sample sequential cytology thin-layer cell sample slide preparation system and illustrates the orientation of an air discharge chamber relative to a tray upstacker, according to an embodiment of the subject matter described herein.

FIG. 23 illustrates an exemplary top right isometric view of the system 10 and illustrates the orientation of the air discharge chamber 40 relative to the tray upstacker 38. The air discharge chamber 40 is shorter than the tray upstacker 38. As trays 32 are processed and stacked within the tray upstacker 38 and dried via air forced through the air discharge chamber 40 and into the tray air inlet nozzles 120, dried thin-layer cell samples on trays 32 may be removed from the upstacker 38 after they exit from the top of the air discharge chamber 40.

Figure 24:
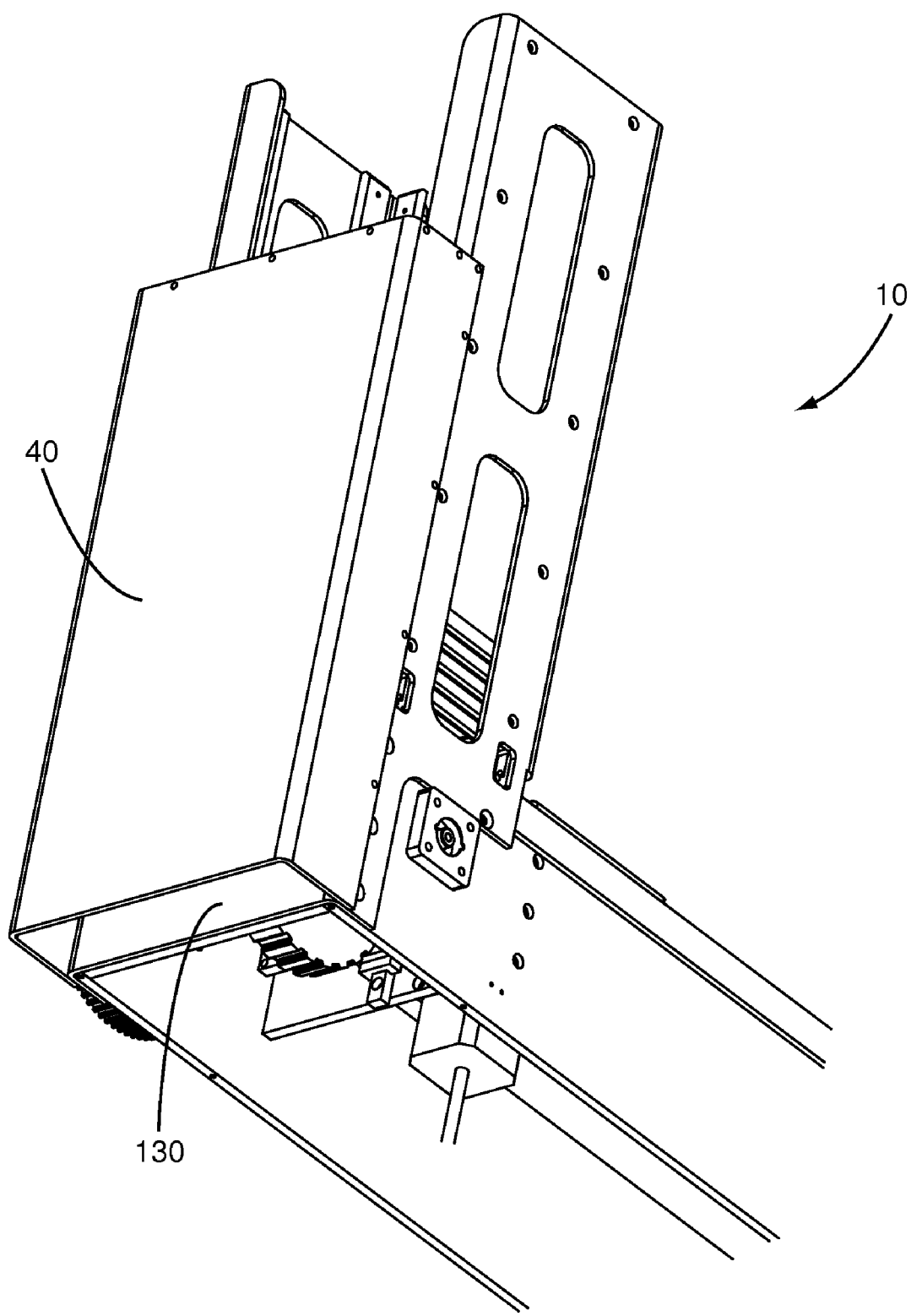
FIG. 24 illustrates an exemplary bottom view of an air discharge chamber, according to an embodiment of the subject matter described herein.

FIG. 24 illustrates an exemplary bottom view of the air discharge chamber 40. An air inlet duct 130 is provided. Air may be forced into the air discharge chamber 40 via the air inlet duct 130 for drying the thin-layer cell samples. As described above, the air which is forced into the air discharge chamber 40 may be treated for moisture or temperature to adjust for ambient conditions to expedite drying of the thin-layer cell samples.

Figure 25:
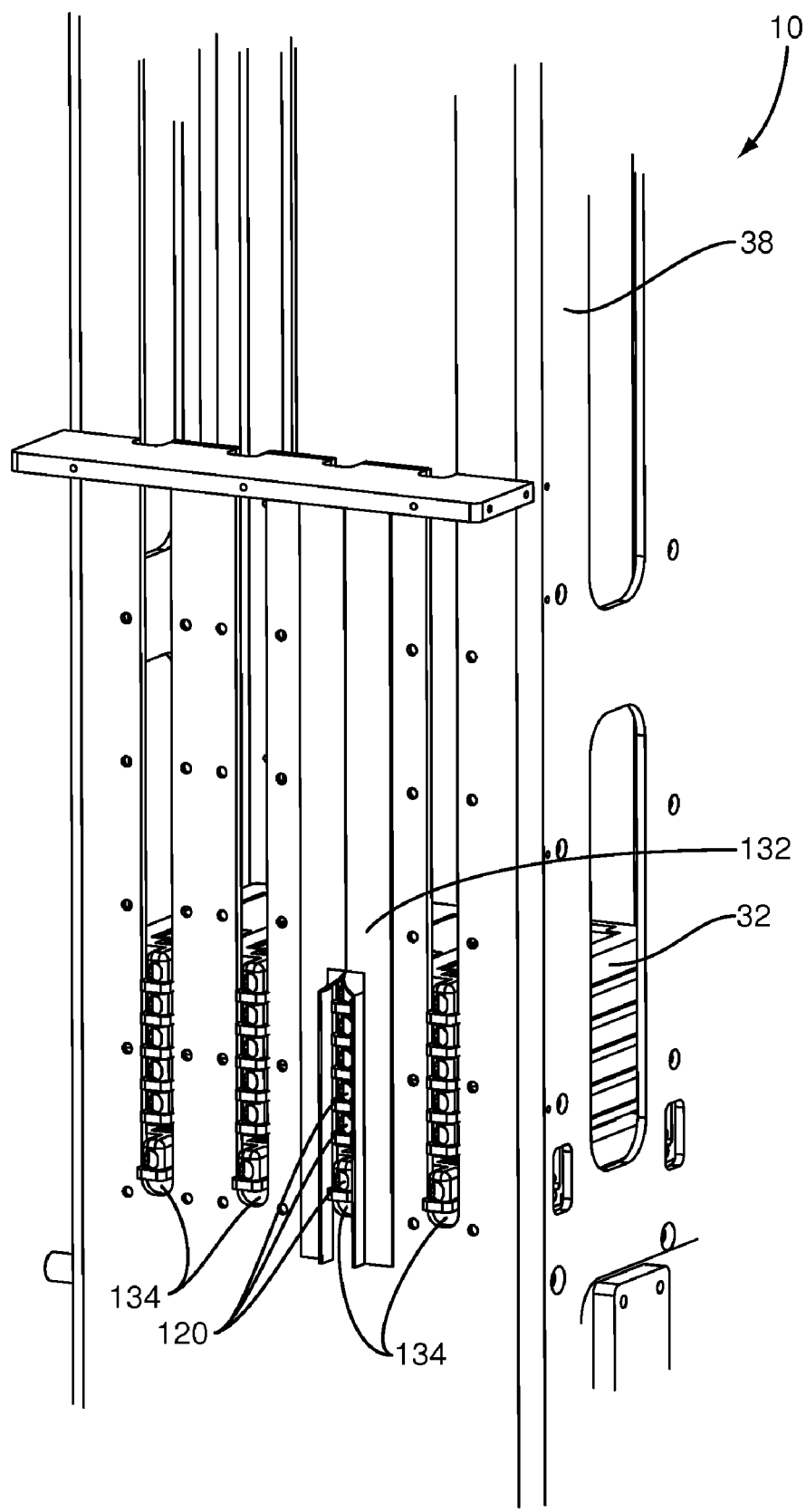
FIG. 25 illustrates an exemplary tray upstacker without an air discharge chamber attached to illustrate an exemplary approach to sealing tray air inlet nozzles within the discharge chamber, according to an embodiment of the subject matter described herein.

FIG. 25 illustrates the tray upstacker 38 without the air discharge chamber 40 attached to illustrate an exemplary approach for directing air from the air discharge chamber 40 into the tray air inlet nozzles 120. A pair of rubber seal strips 132 cover air chamber discharge slits 134 and are deformed and opened by the tray air inlet nozzles 120 to form a seal around the air inlet nozzles 120 and to allow air to enter the tray air inlet nozzles 120. Above the stack of trays 32, the rubber seal strips close to prevent air from leaking out of the air discharge chamber 40. Accordingly, air may be forced from the air discharge chamber 40 and into the tray air inlet nozzles 120 to dry the thin-layer cell samples. Only one pair of rubber seal strips 132 is illustrated for illustrative purposes only and to show that the rubber seal strips 132 are placed in association with air chamber discharge slits 134, which align vertically with the tray air inlet nozzles 120 on each tray 32. The rubber seal strips 132 are placed over each air chamber discharge slit 134 in operation of the system 10.

Figure 26:
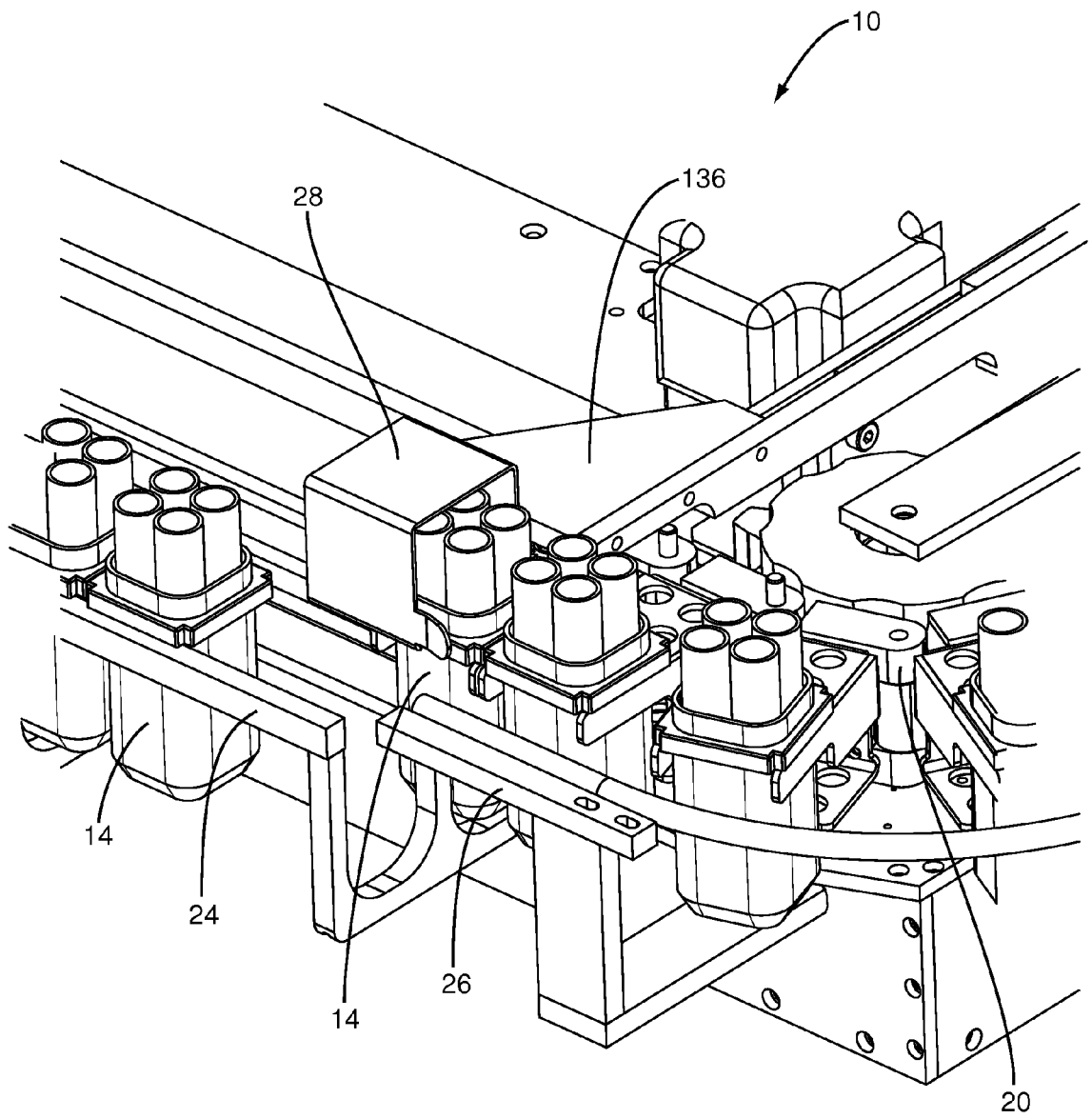
FIG. 26 illustrates an exemplary robotic rack discharge arm that is used to route processed cell samples within tube racks into a tube rack discharge track, according to an embodiment of the subject matter described herein.

FIG. 26 illustrates an exemplary robotic rack discharge arm 136 that is used to route processed cell samples within the tube racks 14 into the tube discharge track 24. The robotic rack discharge arm 136 is the fourth robotic arm used within the system 10 and is a two-axis robotic arm. The robotic rack discharge arm 136 is associated with the rack discharge bracket 28. As the tube rack 14 moves along the tube conveyor 20, it moves into a position underneath the rack discharge bracket 28. As will be described in more detail below, the rack discharge arm 136 actuates to push the tube rack 14 off of the tube conveyor 20 and onto the tube discharge track 24.

Figure 27:
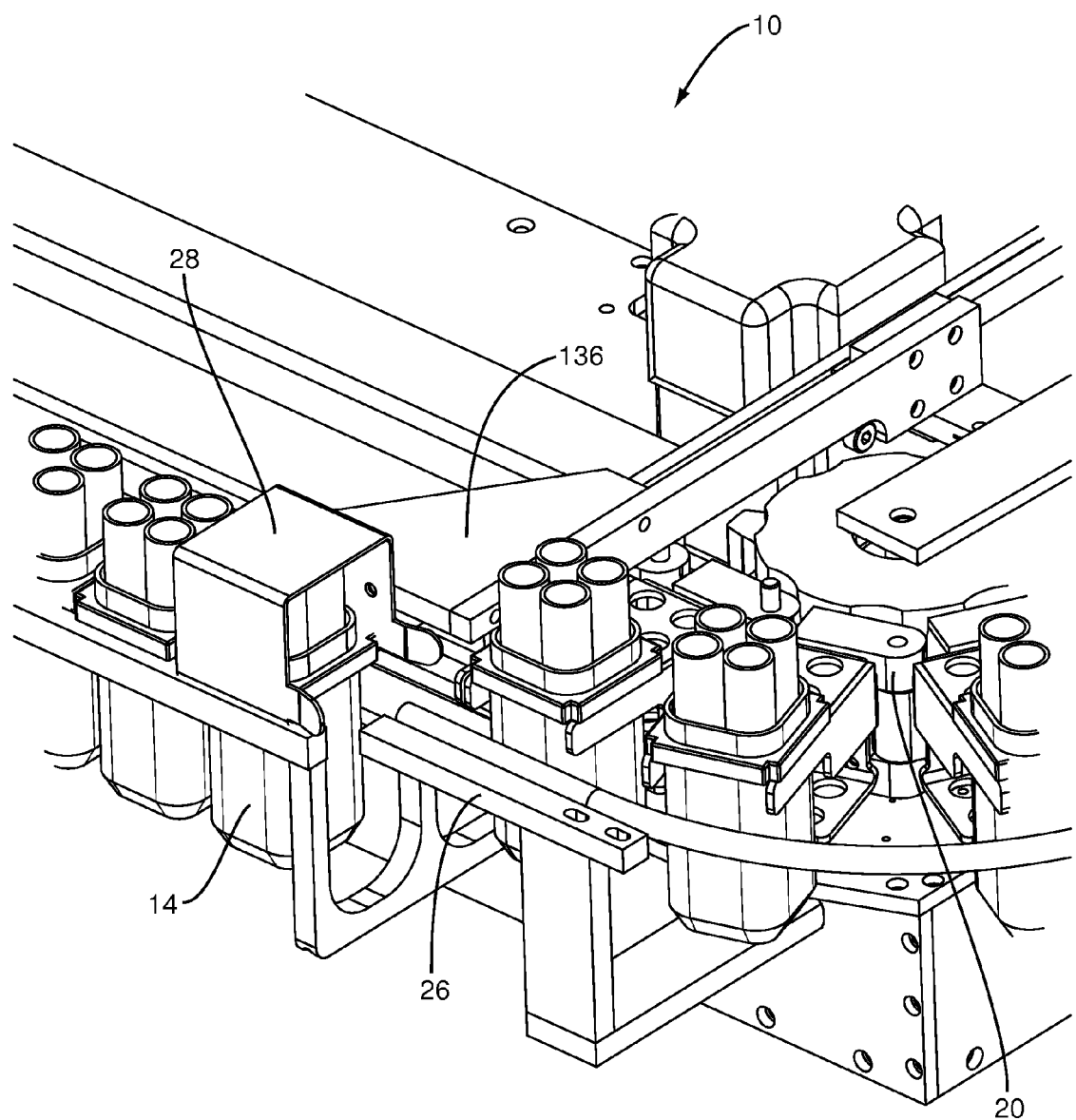
FIG. 27 illustrates an exemplary tube rack positioned within a tube rack discharge track after a rack discharge arm has actuated to push the tube rack from a tube conveyor onto the tube rack discharge track, according to an embodiment of the subject matter described herein.

FIG. 27 illustrates the exemplary tube rack 14 positioned within the tube discharge track 24 after the rack discharge arm 136 has actuated to push the tube rack 14 from the tube conveyor 20 onto the tube discharge track 24.

Figure 28:
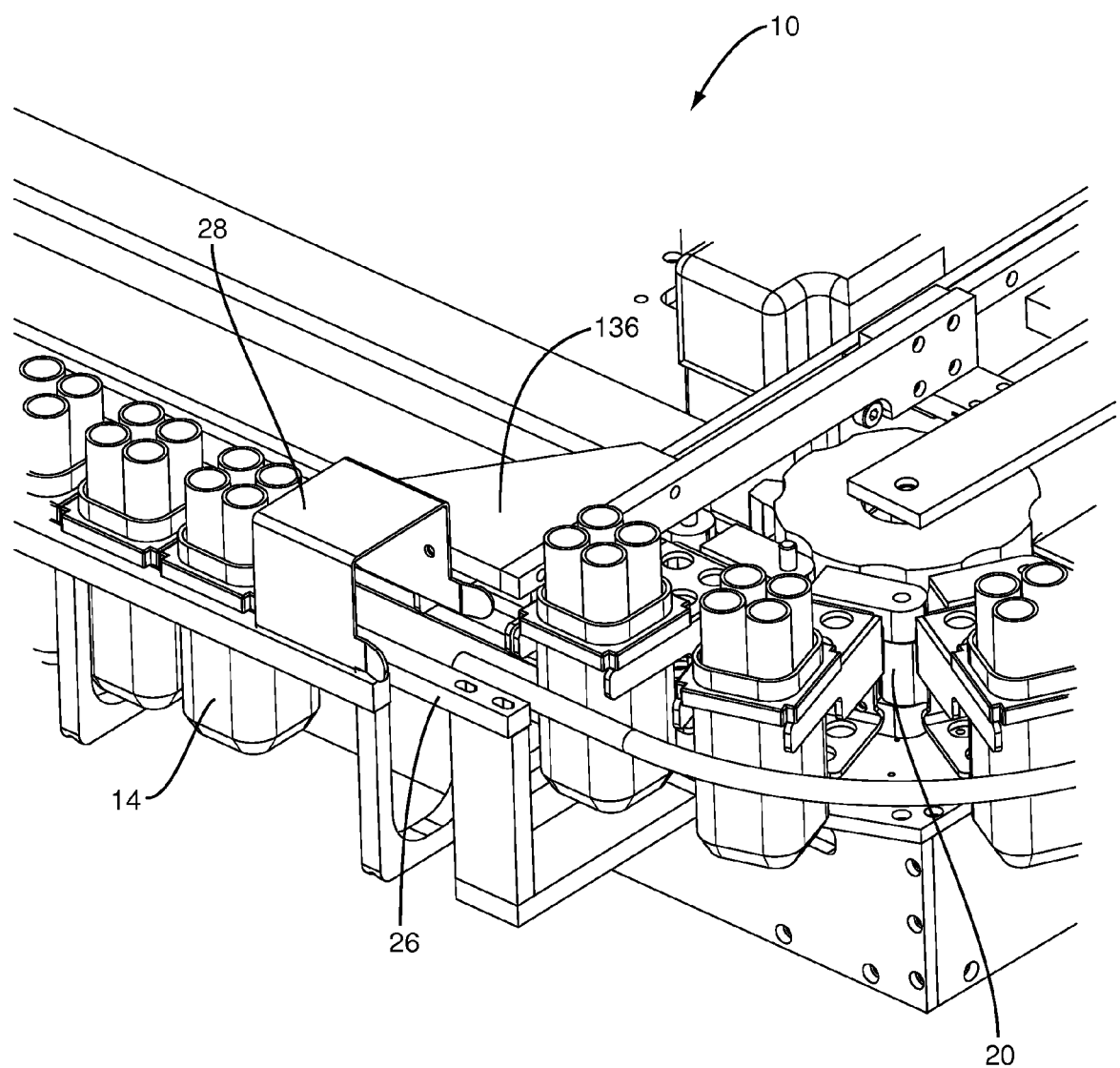
FIG. 28 illustrates an exemplary tube rack after a tube rack has been pushed by a rack advance arm from under a rack discharge bracket, according to an embodiment of the subject matter described herein.

FIG. 28 illustrates the exemplary tube rack 14 after the tube rack 14 has been pushed by the rack advance arm 26 from under the rack discharge bracket 28. The rack discharge arm 136 may then be retracted, thereby pulling the rack discharge bracket 28 back into a position above the tube conveyor 20 and in alignment with the next tube rack 14. The process repeats to remove the tube racks 14 from the tube conveyor 20. As described above, as tube racks 14 are removed from the tube conveyor 20, new tube racks 14 with new samples may be placed onto the tube conveyor 20 for processing.

Those skilled in the art will recognize improvements and modifications to the preferred embodiments of the present invention. All such improvements and modifications are considered within the scope of the concepts disclosed herein and the claims that follow.

What is claimed is:

1. An automated system for thin-layer cell sample slide preparation without human intervention, comprising:
    a cell pellet level detection probe adapted to derive a cell sample measurement from a cell sample;
    a control subsystem adapted to determine an estimation of total cellularity of the cell sample based upon measuring the size of a cell pellet of the cell sample within a centrifuge tube; and
    a fluid control subsystem adapted to:
        dispense a volume of diluent to the cell sample based upon the estimation of total cellularity of the cell sample to form a cell suspension with a predetermined cell concentration; and
        dispense a volume of the cell suspension on a sample slide suitable to form a thin-layer cell sample slide preparation.

2. The automated system of claim 1, wherein the fluid control subsystem is further adapted to dispense the cell suspension on the sample slide as a pattern.

3. The automated system of claim 2, wherein the pattern further comprises at least one of a repeated square pattern, a repeated circular pattern, a repeated rectangular pattern, and a discrete line pattern.

4. The automated system of claim 1, further comprising a conveyor subsystem adapted to automatically move the cell sample from the cell pellet level detection probe to the fluid control subsystem.

5. The automated system of claim 1, further comprising a sample tracking subsystem adapted to track the cell sample during the thin-layer cell sample slide preparation.

6. The automated system of claim 5, wherein the sample tracking subsystem further comprises a barcode reader adapted to read a barcode associated with the cell sample.

7. The automated system of claim 6, wherein the sample tracking subsystem further comprises a label printer adapted to print a label associated with the cell sample.

8. The automated system of claim 7, wherein the sample tracking subsystem further comprises a label handling subsystem adapted to retrieve the label from the label printer and to place the label on the sample slide associated with the cell sample.

9. The automated system of claim 1, further comprising a sample drying subsystem adapted to dry the thin-layer cell sample slide preparation on the sample slide.

10. The automated system of claim 9, wherein the sample drying subsystem further comprises an air discharge chamber adapted to provide a positive air pressure at an interface with a sample tray including the sample slide.

11. The automated system of claim 1, wherein the cell pellet level detection probe is further adapted to measure a height of the cell pellet of the cell sample within a centrifuge tube.

12. The automated system of claim 11, wherein the cell pellet level detection probe further comprises at least one of an ultrasonic level detection probe and a photometric level detection probe.

13. The automated system of claim 1, wherein the control subsystem is further adapted to determine a volume of the cell pellet of the cell sample.

14. The automated system of claim 13, wherein the control subsystem is further adapted to determine the estimation of total cellularity of the cell sample from the volume of the cell sample.

15. The automated system of claim 1, wherein the control subsystem is further adapted to determine the volume of the diluent to dispense to a centrifuge tube based upon the estimation of total cellularity of the cell sample.

16. The automated system of claim 1, wherein the control subsystem is adapted to dispense the cell suspension by being adapted to dispense the cell suspension and an adherent on the sample slide.

17. The automated system of claim 16, wherein the adherent is pre-applied directly on a surface of the sample slide before the cell suspension is dispensed on the sample slide.

18. The automated system of claim 16, wherein the control subsystem is adapted to dispense the cell suspension and the adherent on the sample slide by being adapted to:
    dispense the adherent directly on a surface of the sample slide; and
    dispense the cell suspension onto the adherent on the surface of the sample slide thereafter.

19. The automated system of claim 16, wherein the control subsystem is adapted to dispense the cell suspension and the adherent on the sample slide by being adapted to:
    combine a volume of the cell suspension and a volume of cell adherent based upon the estimation of total cellularity of the cell sample to form a cell mixture with a predetermined cell concentration; and
    dispense the cell mixture directly on a surface of the sample slide suitable to form a thin-layer cell sample slide preparation.

20. The automated system of claim 19, wherein the control subsystem is further adapted to determine the volume of the cell suspension to combine with the volume of the cell adherent.

21. The automated system of claim 19, wherein the control system is further adapted to combine the volume of the cell suspension and the volume of the cell adherent within a transfer tube.

22. The automated system of claim 21, wherein the control subsystem is further adapted to dispense the volume of the diluent to a centrifuge tube including the cell pellet to form the cell suspension.

23. The automated system of claim 1, wherein the volume of diluent is mixed with the cell sample to form the cell suspension.

* * * * *